US006767418B1

(12) United States Patent
Zhang et al.

(10) Patent No.: US 6,767,418 B1
(45) Date of Patent: Jul. 27, 2004

(54) TI-ZR TYPE ALLOY AND MEDICAL APPLIANCE FORMED THEREOF

(75) Inventors: Tao Zhang, Miyagi-ken (JP); Kazuya Sato, Sendai (JP); Kei Kurosaka, Sendai (JP); Yuzi Ogata, Sendai (JP); Xinmin Wang, Sendai (JP); Takashi Kaneko, Nakai-machi (JP); Yuu Kasori, Kanagawa-ken (JP)

(73) Assignees: Terumo Kabushiki Kaisha, Tokyo (JP); Japan Basic Material Co., Ltd., Sendai (JP); Akihisa Inoue, Sendai (JP)

( * ) Notice: Subject to any disclaimer, the term of this patent is extended or adjusted under 35 U.S.C. 154(b) by 0 days.

(21) Appl. No.: 09/551,171

(22) Filed: Apr. 17, 2000

(30) Foreign Application Priority Data

Apr. 23, 1999 (JP) .......................................... 11-116225
Dec. 28, 1999 (JP) .......................................... 11-375057
Dec. 28, 1999 (JP) .......................................... 11-375058

(51) Int. Cl.$^7$ ............................................. C22C 14/00
(52) U.S. Cl. ........................ 148/421; 420/417; 420/422; 623/23.7; 623/23.71; 623/900
(58) Field of Search ........................ 420/417, 422; 148/421; 623/23.7, 23.71, 900

(56) References Cited

U.S. PATENT DOCUMENTS

| | | | |
|---|---|---|---|
| 4,876,126 A | 10/1989 | Takemura et al. | |
| 4,925,445 A | 5/1990 | Sakamoto et al. | |
| 5,037,438 A | 8/1991 | Davidson | |
| 5,152,794 A | 10/1992 | Davidson | |
| 5,545,227 A | * 8/1996 | Davidson et al. | 623/23.53 |
| 5,573,401 A | * 11/1996 | Davidson et al. | 433/201.1 |
| 5,725,572 A | 3/1998 | Lam et al. | |
| 5,837,313 A | * 11/1998 | Ding et al. | 427/2.21 |
| 5,871,595 A | 2/1999 | Ahmed et al. | |
| 5,879,381 A | 3/1999 | Moriuchi et al. | |
| 5,888,201 A | 3/1999 | Stinson et al. | |

FOREIGN PATENT DOCUMENTS

| | | |
|---|---|---|
| EP | 0437079 B1 | 7/1991 |
| EP | 0437079 A1 | 7/1991 |
| EP | 0601804 A1 | 6/1994 |
| EP | 0810374 A2 | 12/1997 |
| EP | 0832618 A1 | 4/1998 |
| JP | 62-20827 | 5/1987 |
| JP | 2-24550 | 5/1990 |
| JP | 3-15914 | 3/1991 |
| JP | 5-269192 | 10/1993 |
| JP | 7-188876 | 7/1995 |
| JP | 8-16256 | 2/1996 |
| JP | 10-211184 | 8/1998 |
| WO | WO93/19804 | 10/1993 |
| WO | WO95/25183 | 9/1995 |
| WO | WO95/34251 | 12/1995 |

* cited by examiner

Primary Examiner—Andrew Oltmans
(74) Attorney, Agent, or Firm—Burns, Doane, Swecker & Mathis, LLP

(57) ABSTRACT

A Ti—Zr type alloy manifesting excellent plastic workability at normal temperature fit for the use in general industry, allowing improvement in corrosion resistance fit for the use in medical treatment, offering improved corrosion resistance in an acidic solution, particularly a HCl solution, and having flexibility as evinced by a low Young's modulus on a par with a bone; and a medical appliance such as a guide wire to be directly inserted into a blood vessel of a human body under the X-ray fluoroscopy and a stent retained in a human body for a long time, which are made of the Ti—Zr type alloy are provided. The Ti—Zr type alloy of the present invention consists of 25 to 50% by weight of Ti, 25 to 60% by weight of Zr, 5 to 30% by weight of Nb, and 5 to 40% by weight of Ta, provided that the weight ratio of Zr to Ti be in the range of 0.5 to 1.5 and the weight ratio of Nb to Ta be in the range of 0.125 to 1.5. The medical appliance of the present invention comprises a part formed of a Ti—Zr type alloy which consists of 25 to 50% by weight of Ti, 25 to 60% by weight of Zr, 5 to 30% by weight of Nb, and 5 to 40% by weight of Ta, provided that the weight ratio of Zr to Ti fall in the range of 0.5 to 1.5 and the weight ratio of Nb to Ta fall in the range of 0.125 to 1.5.

20 Claims, 11 Drawing Sheets

41 42 43 44 45 46 41 47

41    43 44 45 46 41

TI-ZR TYPE ALLOY AND MEDICAL APPLIANCE FORMED THEREOF

BACKGROUND OF THE INVENTION

1. Field of the Invention

This invention relates to a Ti—Zr type alloy which possesses exceptionally high strength and yet manifests low Young's modulus, exhibits sufficient malleability required for the use in structural members, and further excels in plastic workability.

This invention also relates to a medical appliance including a guide wire, a stent, a ventricular assisting device and a catheter which is formed of a Ti—Zr type alloy and used for therapeutic acts under X-ray fluoroscopy represented by a percutaneous transluminal angioplasty (PTA), for example, prevailing in such a medical field as radiology, cardiovascular internal medicine and surgical medicine. More particularly, this invention relates to a medical appliance which is formed of a Ti—Zr type alloy combining sufficient in vivo corrosion resistance, strength and workability necessary for the use in a structural material, biocompatibility, proper contrast and opaqueness, and applicability to MRI.

The Ti—Zr type alloy of this invention comprises Ti, Zr, Nb, and Ta and, optionally such a biocompatible element as Sn, Pd, Pt, and Au, and contains no metallic elements tending to arouse anxiety about toxicity. Thus, the present invention relates to a group of Ti type alloys which is essentially possessed of safety necessary for the use in a grafting material.

These medical appliances will be explained below with reference to a stent, a guide wire, and a ventricular assisting device which are cited as examples of particularly preferable uses found therefor. The alloys mentioned above, in view of their physicochemical properties, should be understood as manifesting additional availability in medical applications and popular applications as well. The alloys ought not to be limited to those uses that are cited by way of illustration in the present specification.

2. Description of the Related Art

A Ti-based alloy excels in corrosion resistance by forming a dense oxide coating of titanium dioxide ($TiO_2$) on the surface thereof in the open air. Owing to its various excellent properties including light weight, great strength, and high specific strength (which is the quotient resulting from the division of the tensile strength by the specific gravity), Ti-based alloys find extensive use as materials for aerospace industry, materials for chemical devices, corrosion-resistant materials for industry utilizing seawater, and materials for consumer products such as camera shutter parts, communication equipment, optical instruments, eyeglass frames, heads, faces, and shafts in wood clubs and iron clubs used in golf. Since the Ti-based alloys mentioned above are in α-phase which exhibits a rigid metallic texture at room temperature, however, they admit of no easy mechanical working such as rolling, forging, or cutting, and are mechanically worked solely in their β-phase region which is separated in a high temperature range and is capable of being machined under the existing circumstances. Moreover, in terms of material, they have the problem of manifesting unusually inferior workability in spite of their fine qualities as in corrosion resistance and strength as compared with other metals. This defect has inhibited conventional Ti-based alloys from finding expansion of their use in general industries.

It has been ascertained as a result of the study pursued to date that titanium (Ti), as well as zirconium (Zr), niobium (Nb), tantalum (Ta), platinum (Pt), and inorganic tin (inorganic Sn) are elements excelling in biocompatibility. They have begun to attract attention as materials for medical appliances. When they are to be used as a materials for medical appliances, however, this use requires them to manifest exacting corrosion resistance as compared with other general industrial uses. Specifically, in the use for medical appliances, since a component separated, even if in a minute amount, by elution from a given material brings adverse effects on a human body to an extent hardly deserving disregard, a material for a medical appliance is required to manifest quality of avoiding elution of a maternal component thereof via an oxide coat manifesting a passive state, even upon contacting with humor or blood. Besides the quality just mentioned above, such a fact as that a material for a medical appliance excels in affinity for the surrounding tissue and approximates closely to a Young's modulus of a living bone constitutes itself a very important element.

For the purpose of attaining the various properties mentioned above, various Ti-based alloys have been reported to date. As typical examples of the Ti-based alloy, an alloy for the used in a dental device which comprises titanium, about 10 to 20% by weight or about 35 to 50% by weight, as the sum of a metal selected from the group consisting of niobium and tantalum, and sufficient zirconium to act as a beta stabilizer and to reduce the rate of transformation of beta structure in the alloy (WO 95/34251); and a titanium alloy containing a first metal, titanium, a second metal selected from the group consisting of zirconium and hafnium, and mixtures thereof, and a third metal selected from the group consisting of niobium, tantalum, vanadium, and mixtures thereof in a prescribed composition (WO 95/25183) may be cited. As regards the former alloy, the weight ratio of zirconium to titanium and the weight ratio of tantalum to niobium has not been referred to anywhere in the relevant official gazette. Specifically, zirconium has been described to account for a proportion of not more than 18% by weight most preferably, tantalum is referred to as accounting for a total proportion in conjunction with niobium and allowing a part of niobium to be substituted with tantalum, and the proportion of tantalum for the most preferable alloy has been stated to be zero. The alloy of this composition is deficient in malleability and proof stress, as well as in corrosion resistance which is expected to be exceptionally strong.

The latter alloy, either in the form of an oxide or on being oxidized, is allowed to form a cermet or ceramic body and is enabled to acquire an expected working efficiency by heating the alloy in a certain temperature range and oxidizing the heated alloy with an oxidant gas thereby altering the quality thereof. The alloy disclosed in WO 95/25183, however, has the problem of failing to manifest a fine beta phase at the time of forming the alloy, revealing deficiency in plasticity and workability at normal temperature, and offering inferior corrosion resistance.

Thus, the development of a Ti-based alloy which has high strength, outstanding corrosion resistance and acid resistance, easy workability, and a low Young's modulus, particularly a Young's modulus close to that of a living bone has been earnestly yearned for. None of the alloys perfected to date, however, satisfies all these properties.

Incidentally, medical appliances using various metals led by the Ti-based alloys have been now in use. A stent, for example, is a hollow cylindrical article which is applied to interiors of a urinary tract, a bile duct, an esophagus, and a nephric tubule as well as a blood vessel with an object of dilating a narrow intracorporeal vessel. As the materials for the stent retaining intracorporeally for a long time, stainless steel (JIS SUS316L), Ta as a pure metal, and Ni—Ti type superelasticity alloys have been already reduced to practice.

Meanwhile, various implant grade Ti-based alloys for the use mainly in artificial joints have been studied from numerous angles. Typically, pure Ti and Ti-6Al-4V alloy (hereinafter all the compositions will be expressed in "weight percent", with the balance assumed to comprise Ti and inevitable impurities, also expressed in "weight percent", unless otherwise specified, in accordance with the general notation of alloy) may be cited. Various Ti-based alloys centering around the β-Ti-based alloys which have been developed to date, however, have not perfectly overcome the problems of corrosion resistance and inclusion of extraneous elements. In view of these problems, attempts have been carried out to manufacture a titanium alloy using Ti, Zr, Sn, Nb, and Ta as constituent components which, as simple elements, has not been recognized to be harmful in vivo. Recently, the improvement of a Ti-based alloy has been proceeded. For example, EP-A-601,804 proposes an artificial heart and an artificial joint using a Ti-13Zr-13Nb alloy; and U.S. Pat. No. 5,888,201 proposes a self-dilating stent made of a Ti alloy using the Ti-13Zr-13Nb alloy mentioned above. Further, JP-B-08-16,256 has proposed a Ti-15Zr-4Nb-4Ta-0.2Pd alloy and a Ti-15Sn-4Nb-2Ta-0.2Pd alloy intended for the use in a long-term implanting material and U.S. Pat. No. 5,871,595 has proposed a Ti-29Nb-13Ta-4.6Zr alloy for the use as an implanting material. These alloys are characterized by containing Ti in a weight ratio of not less than 50% by weight. Further, since they are contemplated as a structural material in alloy designing, they have been awarded no due consideration about opaqueness to X-ray. For the stent which directs due consideration to the importance of contrast and opaqueness to X-ray, the provision of a radioopaque marker made of a noble metal (U.S. Pat. No. 5,725,572) and the use of a clad material formed of a noble metal and stainless steel (WO 93/19804) have been proposed. These articles use stainless steel (JIS SUS316L), primarily as the material on account of precision workability and strength. It may be concluded that these articles have not been awarded due consideration of the safety for the use as a long-term implanting material because they still have to solve the problem that the stainless steel itself is susceptible to corrosion, the problem that the plating yields to pinhole corrosion, the problem that the combination with a different metal entails galvanic corrosion, and etc.

Zr alloys, in addition to the Ti-based alloys, have been studied about the application to a medical appliance as a high biocompatible alloy. For example, U.S. Pat. No. 5,258,022 discloses an artificial cardiac valve which contains Zr as a main component thereof with regard to the blood compatibility of zirconium oxide. Recent studies and JP-A-07-188,876 disclose a Zr30Ti20Al25Pd25 alloy (atomic percent) as a Zr-based metallic glass; and JP-A-10-211,184 discloses a Zr60Al15Ni15Cu5Co5 alloy (atomic percent). These alloys are Zr-based amorphous alloys utilizing its corrosion resistance and non-magnetism. The manufacture of these amorphous alloys has been subjected to the restriction that such special methods of production as a liquid quenching method and a powder molding method should be adopted.

The titanium alloys and the zirconia alloys, as described above, respectively contain Ti and Zr as a main component in an amount of not less than 50% by weight. These alloys, on account of outstanding corrosion resistance, have been considered as an important biocompatible material and have been researched for further development. It, however, has been an universally known fact that they are deficient in workability and in cutting efficiency as compared with ordinary stainless steel. Further, since they have been designed as materials for an artificial joint and an artificial heart, they have not been awarded due consideration of contrast and opaqueness to X-ray. As regards the demands imposed in recent years on medical appliances, the popularization of a magnetic resonance imaging (MRI) apparatus has reached the point of urging the necessity of avoiding exertion of an influence on the image of MRI.

SUMMARY OF THE INVENTION

This invention, which has been initiated in view of the problems encountered by the related arts as described above, has an object of overcoming these problems.

An object of this invention, therefore, is to provide a Ti—Zr type alloy for the use in general industry which combines high strength ($\sigma f$) at normal temperature and a low Young's modulus (E), i.e. high elasticity, and consequently excels in plasticity and workability at normal temperature, and also excels in corrosion resistance.

Another object of this invention is to provide a Ti—Zr type alloy for the medical use which excels in plasticity, workability, and corrosion resistance at normal temperature, and also has excellent affinity with a biological tissue.

Further object of this invention is to provide, on the assumption of in vivo use and direct exposure to humor, a medical appliance formed of a novel improved Ti type alloy which exhibits high safety enough to permit protracted retention on or in the human body.

Another object of this invention is to provide a medical appliance formed of a novel improved Ti type alloy which comprises such biocompatible elements as Ti, Zr, Nb, and Ta and excludes any metallic element having a possibility of toxicity and, therefore, can provide essentially a safety necessary for a transplanting material, manifest high strength and easy workability, and excels in biocompatibility.

Yet another object of this invention is to provide a medical appliance formed of a novel Ti type alloy which exhibits a proper contrast and opaqueness to X-ray under X-ray fluoroscopy in addition to the advantages mentioned above, and particularly to provide such a medical appliance as a guide wire, a catheter, a stent, a stent graft, a venous filter, and an artificial blood vessel which demand a proper contrast and opaqueness as an added value.

Still another object of this invention is to provide a medical appliance which, in addition to the advantages as mentioned above, affects no adverse effects on an image produced in the diagnostic imaging by magnetic resonance imaging. A left ventricular assisting device in particular demands a metallic material excelling in workability because it requires to form a blood pass which is non-magnetic and excels in blood compatibility. The present object, therefore, resides in providing a metallic material satisfying these demands and a medical appliance formed of such a metallic material.

The present inventors, as a result of a diligent study pursued in search of a Ti—Zr type alloy capable of accomplishing the objects mentioned above, have found that a Ti—Zr type quaternary alloy formed of Ti, Zr, Nb, and Ta in a specific composition excels in plasticity and workability at normal temperature and also excels in affinity with a biological tissue. This invention has been perfected based on the knowledge mentioned above.

Specifically, the objects mentioned above can be accomplished by a Ti—Zr type alloy which consists of 25 to 50% by weight of Ti, 25 to 60% by weight of Zr, 5 to 30% by weight of Nb, and 5 to 40% by weight of Ta, provided that the weight ratio of Zr to Ti be in the range of 0.5 to 1.5 and the weight ratio of Nb to Ta be in the range of 0.125 to 1.5.

Further, the present inventors, as the first step toward developing a medical appliance formed of a Ti type alloy having expected properties with a view to solving the problems mentioned above, have launched on the basic designing of an alloy. Both pure Ti and pure Zr are such materials as enabled to exhibit excellent corrosion resistance by forming a dense oxide coat and offer resistance to almost all chemicals. As a result of the detail study performed by the present inventors, it has been found that the corrosion resistance exhibited by pure Ti and pure Zr in various chemicals is complementary in nature. For example, pure Ti is corroded and pure Zr is hardly corroded in inorganic acids like boiling hydrochloric acid and sulfuric acid; and pure Ti is not corroded and pure Zr is corroded in inorganic chloride like an aqueous 30% by weight ferric chloride solution. The combination of the two elements, Ti and Zr, can be expected to provide an alloy having the strongest corrosion resistance. When either of Ti and Zr is adopted as a mother phase of an alloy, a possibility that the quality of either of the two elements will manifest preferentially is conceivable. From the study as mentioned above, using as a starting point a mother alloy containing mutually satisfactorily compatible Ti and Zr in nearly equal quantities, manufacturing a Ti—Zr type alloy having suitably incorporated therein such biocompatible elements as Nb and Ta, and carefully examining the alloy with respect to physical properties and characteristics required by a relevant medical appliance such as, for example, contrast and opaqueness to X-ray, the present inventors have finally discovered a group of novel Ti—Zr type alloys capable of attaining the objects mentioned above.

Besides the knowledge mentioned above, the present inventors have also found that Zr and Sn are suitably interchangeable in their combination with Ti. To be specific, they have found that in the alloys using Ti, Zr, Nb, and Ta in a basic composition thereof, a group of Ti—Zr type alloys having a part of Zr substituted with Sn is similarly suitable as a material for a medical appliance. As a matter of course, such elements as H, O, N, Fe, C, Pd, Ru, and Ni which are inevitably incorporated as impurities originating in the materials of pure Ti and pure Zr can be contained in the alloy in amounts falling within a range which causes to inhibit desired properties. Specifically, industrial grade pure Ti which is used as a raw material normally contains elements in an amount of not more than 0.5% by weight, though depending on the grade of this element. Among these elements, such interstitial elements as C, N, and O which have no toxicity may be positively contained therein. In this case, as respects the ranges incapable of impairing the physical properties of the alloy, the content of each the interstitial elements and impurities does not preferably exceed 0.5% by weight. Actually, since the Ti—Zr type alloy of this invention basically uses such non-magnetic materials as Ti, Zr, Nb, Ta, and Sn, the produced Ti—Zr type alloy is likewise non-magnetic and the medical appliances formed thereof produce no effects on the image by magnetic resonance imaging. This quality of repelling a magnet results in imparting an important property to such a left ventricular assisting device as using magnetic force as a driving force.

The objects of this invention mentioned above can be accomplished by a medical appliance having a part which consists of 25 to 50% by weight of Ti, 25 to 60% by weight of Zr, 5 to 30% by weight of Nb, and 5 to 40% by weight of Ta, provided that the weight ratio of Zr to Ti be in the range of 0.5 to 1.5 and the weight ratio of Nb to Ta be in the range of 0.125 to 1.5.

The Ti—Zr type alloy of this invention consists of 25 to 50% by weight of Ti, 25 to 60% by weight of Zr, 5 to 30% by weight of Nb, and 5 to 40% by weight of Ta, provided that the weight ratio of Zr to Ti be in the range of 0.5 to 1.5 and the weight ratio of Nb to Ta be in the range of 0.125 to 1.5. Since the metallic texture of the Ti—Zr type alloy of this invention, therefore, is allowed to assume a, β-phase at normal temperature without requiring any special heat-treatment in spite of using Ti and Zr as main components, the alloy manifests exceptionally fine workability fit for being rolled, cast, or mechanically processed at normal temperature and further exhibits remarkably excellent plastic workability at normal temperature. Thus, this alloy guides to a new Ti-based alloy as a material for general industry. The alloy is an optimum alloy for medical uses because all the component elements Zr, Ta, and Nb are capable of forming a dense powerful oxide coat and are excellent in in vivo affinity.

Further, a Ti—Zr type alloy having at least either of Nb or Ta in the Ti—Zr type quaternary alloy mentioned above substituted by at least one first substituent element selected from the group consisting of Ni, Cu, Pd, Pt, Al, Si, Cr, Mn, Co, V, Fe, Ag, Au, Sn, Mo, Hf, Zn, Ga, W, Tc, Ru, Rh, Cd, and In; and a Ti—Zr type alloy having at least one first additive element selected from the group consisting of Ni, Cu, Pd, Pt, Al, Si, Cr, Mn, Co, O, N, V, Fe, Ag, Au, Sn, Mo, and Hf in an amount in the range of 0.01 to 5% by weight, based on the total weight of the component elements additionally incorporating therein can be used as a Ti—Zr type alloy both for general industry and medical treatment because of their outstanding corrosion resistance and acid resistance of the mother materials and the mechanical strengths of the mother materials.

The medical appliance of this invention excels in biocompatibility and can be used as a long-term in vivo implanting material because they are formed of a novel Ti type alloy having as the main components thereof such metals as Ti, Zr, Nb, and Ta which are not harmful to a biological tissue. Further, by limiting the contents of Ti and Zr and restricting the composition ratios of Ta and Nb within specific ranges, the alloy can acquire the strongest corrosion resistance in the history and a low elasticity never attained in conventional alloys and secure high strength and workability. As a result, the medical appliance of this invention enjoys a prominent improvement of the degree of freedom in the designing. They can contribute to the enhancement of productivity and the reduction of cost concerning such medical appliances as artificial joints, artificial hearts, prosthesis, artificial blood vessels, artificial corneas, tympanic tubes, and pace makers which have been heretofore formed of Ti type materials difficult to be processed mainly on account of biocompatibility. Since the alloy of this invention is possessed of the ability to control a proper contrast and opaqueness to X-ray under X-ray fluoroscopy by properly adjusting the contents of such elements as Ta and Sn which can impart radiolucency, it can be used in a catheter, a stent, a stent graft, and a venous filter under X-ray fluoroscopy, impart proper X-ray contrast and opaqueness thereto, and provide improved medical appliances. Thus, this alloy can contribute to the therapy under the X-ray fluoroscopy so called "interventional radiology".

In addition to the advantages mentioned above, the medical appliance of this invention brings the advantage of avoiding exertion of adverse effects on an image by MRI because it is formed of a Ti—Zr type alloy which is composed of non-magnetic elements. That is, the medical appliance of this invention can provide such a medical appliance as an endoscopic equipment, a forceps, a surgical instrument, and a medical clip which can be used in combination with MRI. At present, the technique called as "MRI intervention" exists, though on the research level. This technique is a technique of conducting diagnosis and therapy by using a catheter and an endoscope under MRI relying on an image of MRI instead of X-ray, and expected to become a therapeutic technique in near future because of the merit of repressing the exposure of the technician to the X-ray. This invention can be expected to provide a medical appliance to be used in the MRI intervention and contribute greatly to the advance of medical treatment.

The above and other objects, features, and advantages of the present invention will become clear from the following description of the preferred embodiments.

DESCRIPTION OF THE PREFERRED EMBODIMENTS

Figure 1:
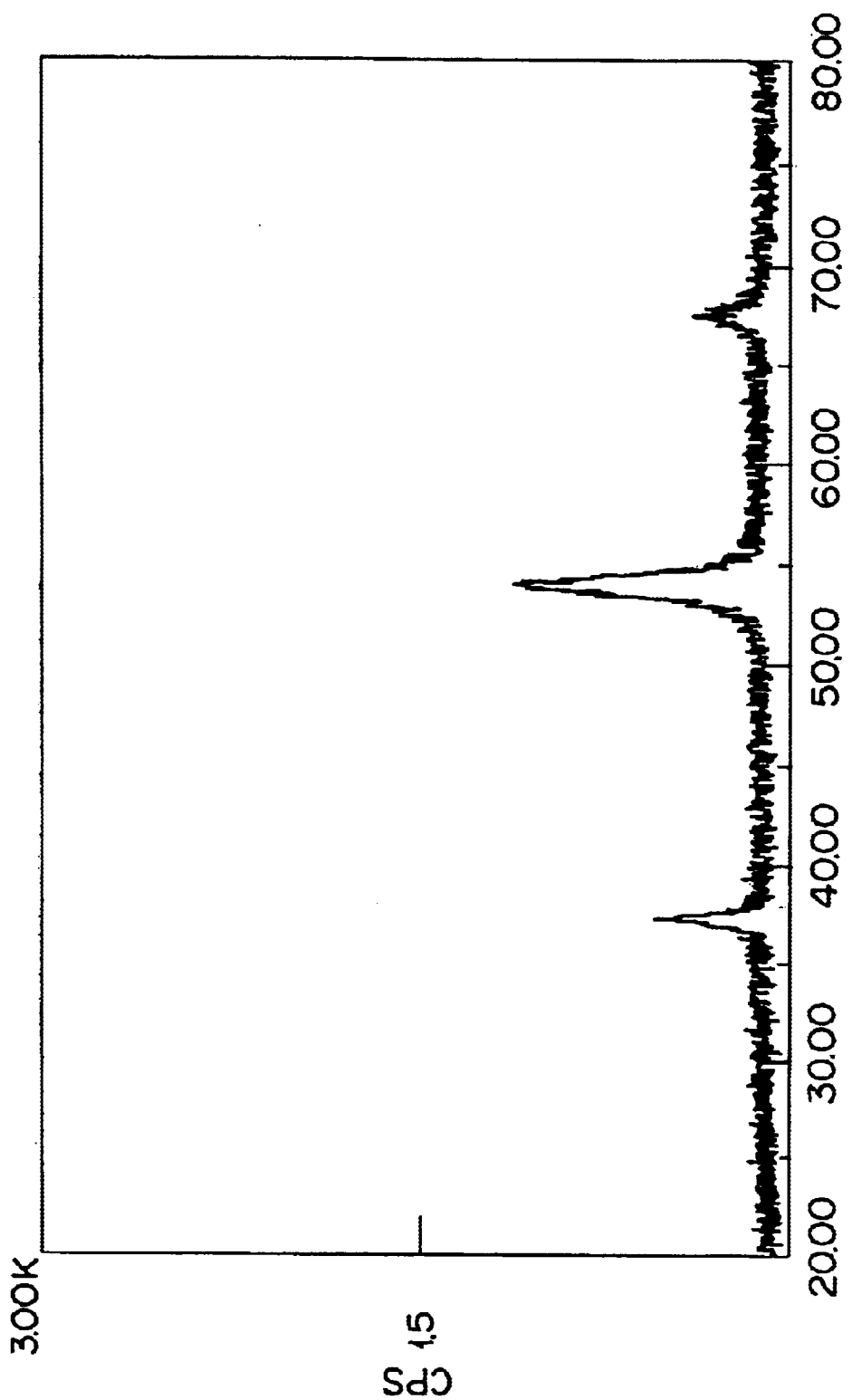
FIG. 1 is an X-ray diffraction graph showing the β-phase of a Ti—Zr type quaternary alloy manufactured in Example 2 (Ti-34.8Zr-11.8Nb-23.0Ta).

Now, this invention will be described in detail below.

According to the first aspect of this invention, a Ti—Zr type alloy which consists of 25 to 50% by weight of Ti, 25 to 60% by weight of Zr, 5 to 30% by weight of Nb, and 5 to 40% by weight of Ta, provided that the weight ratio of Zr to Ti be in the range of 0.5 to 1.5 and the weight ratio of Nb to Ta be in the range of 0.125 to 1.5 is provided. In this aspect, the contents (% by weight) of the component elements are respectively selected so that the sum of the component elements of the alloy, excepting impurities and not more than 5% by weight of additives, may reach 100% by weight.

Among the component elements of the alloy of the first aspect, Ti has been known to assume a hexagonal close-packed lattice structure (α-phase) at normal temperature allowing no expectation for large ductility and, when heated to not less than 882° C., to assume a body-centered cubic lattice structure (β-phase) manifesting larger ductility than the α-phase. Pure Ti (grade 2) has a Young's modulus of 106 Gpa and, at a temperature of not less than 610° C., forms a dense oxide coat of titanium dioxide ($TiO_2$; the same used hereinafter) on the surface thereof. This $TiO_2$ coat shows no change in open air at normal temperature, excels in strength, manifests corrosion resistance, and gives rise to titanium tetrachloride ($TiCl_4$; the same used hereinafter) at a temperature of not less than 300° C. Incidentally, Ti excels in specific strength (which is the quotient resulting from the division of the tensile strength by the specific gravity) and, owing to this characteristic property, finds extensive use in Ti-based alloys. When Ti is transformed into a Ti-based alloy, however, it turns into a solid solution and exerts a large influence on the ductility. If the Ti is deprived of ductility, it would no longer undergo forging which is an important means for improving the cast texture. For the Ti-based alloy to be rated an excellent product, therefore, the plasticity forms an essential condition. At present, unfortunately, the Ti-based alloys on incorporating therein elements of some purposes are frequently embrittled and profoundly degraded in workability to the extent of becoming unusable. It has been found that the defects mentioned above can be overcome by using the quaternary alloy formed of Ti—Zr—Nb—Ta in a specific composition as contemplated by this invention.

In the first aspect, the content of Ti satisfies the following relation with the content of Zr and, at the same time, falls generally in the range of 25 to 50% by weight, preferably in the range of 30 to 40% by weight, and more preferably in the range of 30 to 35% by weight, based on the total weight of the component elements. In this case, if the content of Ti exceeds 50% by weight, the content of Ti would be unduly large and the excess would be at a disadvantage in compelling the deficiency of inherent Ti in plasticity and workability to manifest conspicuously, preventing the alloy itself, like the conventional Ti-based alloy, from being worked at normal temperature, and necessitating addition of steps such as heat-treatment. Conversely, if the content of Ti is less than 25% by weight, the content of Ti would be unduly small and the shortage would be at a disadvantage in not acquiring fully satisfactorily the excellence in strength, specific strength, corrosion resistance, and stability which is derived from Ti, and consequently failing to manifest the excellent quality inherent in Ti. The alloy, therefore, no longer deserves to be called a Ti-based alloy.

Zr as one of the component elements of the alloy of this invention assumes the hexagonal close-packed lattice structure (α-phase) at normal temperature and, when heated to a temperature of not less than 862° C., turns into the body-centered cubic structure (β-phase). Zr forms a dense oxide coat in open air, excels in corrosion resistance, particularly manifesting notably high corrosion resistance as compared with other metals in water at an elevated temperature, and allows no easy reaction in a fused alkali. Zr finds use in various machines because of its fine corrosion resistance and acid resistance. Incidentally, a Young's modulus of pure Zr is 94.5 Gpa.

In the first aspect, Zr has an essential requirement of satisfying the condition that the Zr content be in the range of 25 to 60% by weight, based on the total weight of the component elements and the weight ratio of Zr to Ti be in the range of 0.5 to 1.5. The content of Zr is preferably in the range of 25 to 45% by weight, more preferably in the range of 30 to 35% by weight, based on the total weight of the component elements. The weight ratio of Zr to Ti is preferably in the range of 0.5 to 1.5 and more preferably in the range of 0.8 to 1.2. In this case, if the content of Zr is less than 25% by weight or the weight ratio of Zr to Ti is less than 0.5, the shortage would be at a disadvantage in suffering the α-phase of Ti to separate in the alloy, notably degrading plasticity and workability, increasing a Young's modulus, and degrading the affinity with a biological tissue. In contrast, if the content of Zr exceeds 60% by weight or the weight ratio of Zr to Ti exceeds 1.5, the excess would be likewise at a disadvantage in showing no improvement in corrosion resistance, only increasing the specific gravity of the alloy to be obtained, increasing a Young's modulus, and degrading plasticity and workability. When the content of Zr is set in the specific range mentioned above, Ti produces no change in open air at normal temperature and Zr forms a dense oxide coat and the characteristics of the two elements are synergisticly combined and enabled to manifest fine corrosion resistance and acid resistance.

Then, Nb as one of the component elements of the alloy of this invention manifest ductility, has a Young's modulus of 105 Gpa, exhibits rigidity on a par with that of wrought iron, and excels Ta, another component element of the alloy, in softness. The addition of Nb, therefore, results in imparting flexibility (low elasticity) to the produced alloy. Nb is a metal which forms an oxide coat in open air and manifests corrosion resistance. It is insoluble in an acid other than hydrofluoric acid and also insoluble in an aqueous alkali solution. It finds extensive use as an additive element to various alloys (such as, heat-resistant alloys). When Nb is used as a component element of the Ti—Zr type alloy of this invention, therefore, it cooperates with Zr in improving the alloy in corrosion resistance and acid resistance.

In the aspect described above, Nb has an essential requirement of satisfying the condition that the Nb content be in the range of 5 to 30% by weight, based on the total weight of the component elements and the weight ratio of Nb to Ta be in the range of 0.125 to 1.5. The content of Nb is preferably in the range of 10 to 20% by weight and more preferably in the range of 10 to 15% by weight, based on the total weight of the component elements. The weight ratio of Nb to Ta is preferably in the range of 0.3 to 1.5 and more preferably in the range of 0.5 to 1.0. In this case, if the content of Nb is less than 5% by weight or the weight ratio of Nb to Ta is less than 0.125, the shortage would bring the problem that the produced alloy exhibits no sufficient flexibility, manifests unduly low plasticity, and suffers an increase of a Young's modulus. Conversely, if the Nb content exceeds 30% by weight or the weight ratio of Nb to Ta exceeds 1.5, the excess would be at a disadvantage in disappointing the hope of improving the corrosion resistance and the flexibility, bringing no discernible improvement in corrosion resistance, simply increasing the specific gravity, and failing to improve the affinity with a biological tissue.

Then, Ta which is one of the component elements of the alloy of this invention abounds in ductility and manifests elasticity, like Nb. Ta is a metal which is harder than Nb and has a Young's modulus of 187 Gpa. The addition of Ta, therefore, results in enhancing the elasticity of the alloy and not in imparting flexibility thereto. Further, Ta is a metal which forms an oxide coat in open air and exhibits corrosion resistance. It is characterized by possessing exceptionally strong corrosion resistance. When Ta is used as a component element of the Ti—Zr type alloy of this invention, therefore, it is enabled to cooperate with Zr in improving the corrosion resistance.

In the first aspect, the content of Ta satisfies the aforementioned relation with the content of Nb and, at the same time, accounts for a proportion generally in the range of 5 to 40% by weight, preferably in the range of 10 to 30% by weight, and more preferably in the range of 15 to 25% by weight, based on the total weight of the component elements. In this case, if the content of Ta is less than 5% by weight, the shortage would be at a disadvantage in compelling the produced alloy to acquire an unduly high Young's modulus, lowered ductility, and inferior proof stress. In contrast, if the content of Ta exceeds 40% by weight, the excess would be at a disadvantage in not only disappointing the hope of improving the corrosion resistance but also increasing the specific gravity, inducing gradual loss of the flexibility, and compelling the produced alloy to become brittle and deficient in workability.

The method for producing the Ti—Zr type alloy of this invention does not need to be particularly discriminated but is required only to be capable of producing an alloy having such a specific composition as mentioned above. As typical examples of this method of production, a method which comprises steps of weighing required elements (for example, Ti in the form of sponge titanium and pure titanium, Grades 1 to 4; Zr in the form of sponge zirconium and pure zirconium; Nb in the form of pure niobium; and Ta in the form of pure tantalum, each possessing no specifically limited shape and having purity enough to avoid exerting adverse effects on the quality of the produced alloy) in a prescribed composition (% by weight), arc melting the elements in a water-cooled copper hearth, transforming the resultant molten mass into an alloy, and forming the alloy in an ingot; a method which comprises steps of melting the elements in a crucible, transforming the molten mass into an alloy, and atomizing the alloy into a powder; a method which comprises steps of similarly melting the elements and casting the resultant molten mass; a method which comprises steps of levitation melting the elements, transforming the molten mass into an alloy, and forming the alloy in an ingot; such methods as a mechanical alloying method, a sputtering method, and a plasma method which have been generally carried out on a commercial scale; and methods published by various research institutes and reported in literature may be cited.

The Ti—Zr type quaternary alloy of this invention which has a composition in the specified range mentioned above exhibits exceptionally fine workability such that the work of rolling, forging, or mechanical processing can be carried out at normal temperature in spite of the fact that it is an alloy having Ti and Zr as main components thereof because the metallic texture thereof assumes the β-phase at normal temperature. As one example of the metallic texture, an X-ray diffraction diagram illustrating the β-phase of the Ti—Zr type quaternary alloy (Ti-34.8Zr-11.8Nb-23.0Ta) manufactured in Example 2 to be cited herein below is illustrated in FIG. 1.

In this invention, Nb and/or Ta, the component elements of the Ti—Zr type alloy according to the first aspect described above may be substituted by at least one first substituent element selected from the group consisting of Ni, Cu, Pd, Pt, Al, Si, Cr, Mn, Co, V, Fe, Ag, Au, Sn, Mo, Hf, Zn, Ga, W, Tc, Ru, Rh, Cd, and In. The Ti—Zr type alloy having such a composition is novel and, therefore, constitutes itself another aspect of this invention. Specifically, according to the second aspect of this invention, a Ti—Zr type alloy having at least either of Nb or Ta in the Ti—Zr type quaternary alloy mentioned above substituted by at least one first substituent element selected from the group consisting of Ni, Cu, Pd, Pt, Al, Si, Cr, Mn, Co, V, Fe, Ag, Au, Sn, Mo, Hf, Zn, Ga, W, Tc, Ru, Rh, Cd, and In is provided.

In the second aspect mentioned above, the content of the at least one first substituent element may be decided depending on the kind of the first substituent element and the content of the substituted Nb and/or Ta.

Among the first substituent elements which are usable for the substitution for Nb and/or Ta in the alloy of the second aspect mentioned above, Pt, Au, and Pd are elements which excel in corrosion resistance. By having these elements substituted for Nb and/or Ta, it is made possible to promote the improvement of the mother material in corrosion resistance. Since these first substituent elements avoid exerting any adverse effect on a biological tissue and excel in affinity with a biological tissue as well, they can be particularly advantageously used when the alloy of this invention is adopted for medical treatment. Further, though the first substituent elements other than Pt, Au, and Pd are components which are effective in enhancing the mechanical strength of the mother material, they are not suitable for medical treatment because they invariably degrade the corrosion resistance of the produced alloy and manifest inferior affinity with a biological tissue. When the elements other than Pt, Au, and Pd are to be used as the first substituent element, the Ti—Zr type alloy to be produced is used in the products of the general industry such as, for example, marine materials to be exposed to the saline atmosphere (metallic materials such as fishing rod and reel and metallic fishing line), eyeglass frames suffering adhesion of sweat containing salinity, and materials for heads, faces, and shafts in wood clubs and iron clubs for golf which are required to manifest high specific strength.

The composition of the alloy according to the aspect mentioned above does not need to be particularly limited but is required only to satisfy the conditions of composition mentioned above. As typical examples of the composition, the following compositions may be cited.

1) A multi-element alloy of a composition, $Ti_{a1}Zr_{b1}Nb_{c1}$ (at least one first substituent element selected from the group consisting of Ni, Cu, Pd, Pt, Al, Si, Cr, Mn, Co, V, Fe, Ag, Au, Sn, Mo, Hf, Zn, Ga, W, Tc, Ru, Rh, Cd, and $In)_{d1}$ (wherein a1 stands for the content of Ti (% by weight) falling in the range of 25 to 50, b1 for the content of Zr (% by weight) falling in the range of 25 to 60, c1 for the content of Nb (% by weight) falling in the range of 5 to 30, and d1 for the total content of first substituent elements (% by weight) falling in the range of 5 to 40, provided that the ratio, b1/a1, fall in the range of 0.5 to 1.5 and the ratio, c1/d1, in the range of 0.125 to 1.5);

2) A multi-element alloy of a composition, $Ti_{a2}Zr_{b2}$ (at least one first substituent element selected from the group consisting of Ni, Cu, Pd, Pt, Al, Si, Cr, Mn, Co, V, Fe, Ag, Au, Sn, Mo, Hf, Zn, Ga, W, Tc, Ru, Rh, Cd and $In)_{c2}Ta_{d2}$ (wherein a2 stands for the content of Ti (% by weight) falling in the range of 25 to 50, b2 for the content of Zr (% by weight) falling in the range of 25 to 60, c2 for the total content of first substituent elements (% by weight) falling in the range of 5 to 30, and d2 for the content of Ta (% by weight) falling in the range of 5 to 40, provided that the ratio, b2/a2, fall in the range of 0.5 to 1.5 and the ratio, c2/d2, in the range of 0.125 to 1.5); and 3) A multi-element alloy of a composition, $Ti_{a3}Zr_{b3}$ (at least one first substituent element selected from the group consisting of Ni, Cu, Pd, Pt, Al, Si, Cr, Mn, Co, V, Fe, Ag, Au, Sn, Mo, Hf, Zn, Ga, W, Tc, Ru, Rh, Cd, and $In)_{c3+d3}$ (wherein a3 stands for the content of Ti (% by weight) falling in the range of 25 to 50, b3 for the content of Zr (% by weight) falling in the range of 25 to 60, and c3+d3 for the total content of first substituent elements (% by weight) falling in the range of 10 to 50, provided that the ratio, b3/a3, fall in the range of 0.5 to 1.5).

In the second aspect of this invention, the first substituting elements may be suitably selected, depending on the intended use and the expected quality, in due consideration of the properties as mentioned above, as follows.

1. For the use in general industry, where Nb is substituted with one first substituent element, V, Cr, Mn, Fe, Co, Ni, Cu, Zn, Ga, Mo, Tc, Ru, Rh, Pd, Ag, Cd, In, or Sn proves suitable;

2. For the use in general industry, where Nb is substituted with a mixture of two or more first substituent elements, the combinations of Sn—Pt, Cu—Ni, Co—Cr, or Al—V prove suitable;

3. For the use in medical treatment, where Nb is substituted with one first substituent element, V, Cr, Co, Ag, Sn, Au, Pd, Pt, Ni, or Al proves suitable;

4. For the use in medical treatment, where Nb is substituted with a mixture of two or more first substituent elements, the combinations of elements selected from the group consisting of V, Cr, Mo, Pd, Ag, Sn, Pt, and Au prove suitable;

5. For the use in general industry, where Ta is substituted with one first substituent element, V, Cr, Mn, Fe, Co, Ni, Cu, Zn, Ga, Mo, Tc, Ru, Rh, Pd, Ag, Cd, In, or Sn proves suitable;

6. For the use in general industry, where Ta is substituted with a mixture of two or more first substituent elements, the combinations of Al—Ni, Cu—Co, Sn—Pd, and Cu—Al prove suitable;

7. For the use in medical treatment, where Ta is substituted with one first substituent element, V, Cr, Co, Ag, Sn, Au, Pd, Pt, Ni, or Al proves suitable;

8. For the use in medical treatment, where Ta is substituted with a mixture of two or more first substituent elements, the combinations of elements selected from the group consisting of V, Cr, Mo, Pd, Ag, Sn, Pt, and Au prove suitable;

9. For the use in general industry, where Nb and Ta are substituted with one first substituent element, V, Cr, Mn, Fe, Co, Ni, Cu, Zn, Ga, Mo, Tc, Ru, Rh, Pd, Ag, Cd, In, or Sn proves suitable;

10. For the use in general industry, where Nb and Ta are substituted with a mixture of two or more first substituent elements, the combinations of elements selected from the group consisting of V, Cr, Mn, Fe, Co, Ni, Cu, Zn, Ga, Mo, Tc, Ru, Rh, Pd, Ag, Cd, In, and Sn prove suitable;

11. For the use in medical treatment, where Nb and Ta are substituted with one first substituent element, V, Cr, Co, Ag, Sn, Au, Pd, Pt, Ni, or Al proves suitable;

12. For the use in medical treatment, where Nb and Ta are substituted with a mixture of two or more first substituent elements, the combinations of elements selected from the group consisting of V, Cr, Mo, Pd, Ag, Sn, Pt, and Au prove suitable.

The method for producing the Ti—Zr type alloy according to the second aspect of this invention does not need to be particularly discriminated but is required only to be capable of producing an alloy having such a specific composition as mentioned above. As typical examples of this method of production, a method which comprises steps of weighing required elements (for example, Ti in the form of sponge titanium and pure titanium, Grades 1 to 4; Zr in the form of sponge zirconium and pure zirconium; Nb in the form of pure niobium; and Ta in the form of pure tantalum, each possessing no specifically limited shape and having purity enough to avoid exerting adverse effects on the quality of the produced alloy) in a prescribed composition (% by weight), are melting the elements in a water-cooled copper hearth, transforming the resultant molten mass into an alloy, and forming the alloy in an ingot; a method which comprises steps of melting the elements in a crucible, transforming the molten mass into an alloy, and atomizing the alloy into a powder; a method which comprises steps of similarly melting the elements and casting the resultant molten mass; a method which comprises steps of levitation melting the elements, transforming the molten mass into an alloy, and forming the alloy in an ingot; such methods as a mechanical alloying method, a sputtering method, and a plasma method which have been generally carried out on a commercial scale; and methods published by various research institutes and reported in literature may be cited. In this case, the form of an expected first substituent element does not need to be particularly discriminated but may be the same as in any of known methods. For example, Ni may be used in the form of pure nickel, Cu in the form of pure copper, oxygen-free copper, phosphorus deoxidized copper, or tough pitch copper, Al in the form of pure aluminum, and other first substituent elements each in the form of pure metal.

Further, in this invention, the Ti—Zr type alloy according to the first aspect mentioned above may have incorporated therein at least one first additive element selected from the group consisting of Ni, Cu, Pd, Pt, Al, Si, Cr, Mn, Co, O, N, V, Fe, Ag, Au, Sn, Mo, and Hf in an amount in the range of 0.01 to 5% by weight, based on the total weight of the component elements, which Ti—Zr type alloy is also novel, it constitutes itself another aspect of this invention. According to the third aspect of this invention, therefore, a Ti—Zr type alloy of the first aspect of this invention which further comprises at least one first additive element selected from the group consisting of Ni, Cu, Pd, Pt, Al, Si, Cr, Mn, Co, O, N, V, Fe, Ag, Au, Sn, Mo, and Hf in an amount in the range of 0.01 to 5% by weight, based on the total weight of the component elements is provided. By adding such a first additive element as mentioned above in the prescribed proportion to the Ti—Zr type alloy of the first aspect as described above, the mechanical strength of the mother material can be improved. Further, similar to the second aspect, among these first additive elements, Pt, Au, and Pd are elements which excel in corrosion resistance. By incorporating these elements in the alloy, the improvement of the mother material in corrosion resistance can be attained. Since these elements avoid exerting any adverse effect on a biological tissue and excel in affinity with a biological tissue as well, they prove particularly advantageously when the alloy of this invention is used in medical treatment. Further, the additive elements other than Pt, Au, and Pd, though effective in heightening the mechanical strength of the mother material, are invariably deficient in affinity with a biological tissue, and therefore, are not suitable for medical use. When the elements other than Pt, Au, and Pd are to be used as the first additive element, the Ti—Zr type alloy to be obtained are used in the products of the general industry such as, for example, marine materials to be exposed to the saline atmosphere (metallic materials such as fishing rod and reel and metallic fishing line), eyeglass frames suffering adhesion of sweat containing salinity, and materials for heads, faces, and shafts in wood clubs and iron clubs for golf which are required to manifest high specific strength.

In the third aspect mentioned above, the content of the first additive element is essentially in the range of 0.01 to 5% by weight, preferably in the range of 1 to 4% by weight, and more preferably in the range of 2 to 3% by weight, based on the total weight of the component elements. In this case, if the content of the first additive element is less than 0.01% by weight, the shortage would be at a disadvantage in preventing effects obtained by adding the first additive element from being manifested appreciably and suffering the added element to function like the extraneous trace element. Conversely, if the content of the first additive element exceeds 5% by weight, the excess would be at a disadvantage in compelling the produced alloy to manifest a quality different from the expected quality.

In the third aspect mentioned above, the first additive element is at least one member selected from the group consisting of Ni, Cu, Pd, Pt, Al, Si, Cr, Mn, Co, O, N, V, Fe, Ag, Au, Sn, Mo, and Hf and more preferably at least one member selected from the group consisting of Ni, Pd, Cr, Co, and Fe. When a mixture of two or more first additive elements is used, the combination of such elements is varied with the total content of Ti, Zr, Nb, and Ta, the intended use, and the expected properties. For the use in general industry, the combinations of elements selected from the group consisting of Cr, Mo, Ni, and Co, preferably the combinations of Cr and Mo, may be cited. For the use in medical treatment, the combinations of elements selected from the group consisting of Pd, Pt, Au, Sn, Ni, Al, and V, preferably the combinations of elements selected from the group consisting of Pt, Pd, and Sn, prove suitable.

The method for producing the Ti—Zr type alloy according to the above aspect of this invention does not need to be particularly discriminated but is required only to be capable of producing an alloy having such a specific composition as mentioned above. As typical examples of this method of production, a method which comprises steps of weighing required elements (for example, Ti in the form of sponge titanium and pure titanium, Grades 1 to 4; Zr in the form of sponge zirconium and pure zirconium; Nb in the form of pure niobium; and Ta in the form of pure tantalum, each possessing no specifically limited shape and having purity enough to avoid exerting adverse effects on the quality of the produced alloy) in a prescribed composition (% by weight), arc melting the elements in a water-cooled copper hearth, transforming the resultant molten mass into an alloy, and forming the alloy in an ingot; a method which comprises steps of melting the elements in a crucible, transforming the molten mass into an alloy, and atomizing the alloy into a powder; a method which comprises steps of similarly melting the elements and casting the resultant molten mass; a method which comprises steps of levitation melting the elements, transforming the molten mass into an alloy, and forming the alloy in an ingot; such methods as a mechanical alloying method, a sputtering method, and a plasma method which have been generally carried out on a commercial scale; and methods published by various research institutes and reported in literature may be cited. In this case, the form of an expected first additive element does not need to be particularly discriminated but may be the same as in any of known methods. For example, Ni may be used in the form of pure nickel, Cu in the form of pure copper, oxygen-free copper, phosphorus deoxidized copper, or tough pitch copper, Al in the form of pure aluminum, and other first additive elements each in the form of pure metal.

Then, according to the fourth aspect of this invention, a medical appliance which comprises a part formed of the Ti—Zr type alloy according to the first aspect of this invention, i.e., a Ti—Zr type alloy which consists of 25 to 50% by weight of Ti, 25 to 60% by weight of Zr, 5 to 30% by weight of Nb, and 5 to 40% by weight of Ta, provided that the weight ratio of Zr to Ti fall in the range of 0.5 to 1.5 and the weight ratio of Nb to Ta fall in the range of 0.125 to 1.5 is provided. In this aspect described above, the contents (% by weight) of the component elements are respectively selected so that the sum of the component elements of the alloy, excepting impurities and not more than 5% by weight of additives, may reach 100% by weight. This Ti—Zr type alloy, when formed in such a basic composition as described above, can afford a biocompatible alloy which excels in corrosion resistance, avoids the generation of harmful ions, and have both workability and strength. With a view to preventing the quality of either Ti or Zr from prevailing, the weight ratio of Zr to Ti must be adjusted within the range of 0.5 to 1.5. If the weight ratio of Zr to Ti deviates from the range mentioned above, the mother phase would be caused to manifest prominently the quality of either of the elements and would be deprived of cold workability.

Among the component elements which form the alloy according to the fourth aspect, Ti, Zr, Nb, and Ta are as defined respectively in the first aspect as described above.

Further, in the fourth aspect, a part of the Zr component element of the Ti—Zr type alloy may be substituted by Sn. Since the element Sn is capable of enhancing contrast and opaqueness in X-ray photography, the Ti—Zr type alloy having a part of the Zr component element substituted by Sn manifests improved contrast and opaqueness in the X-ray photography and allows the thickness of a finished product to be decreased. In this case, the content of Sn is in the range of 5 to 10% by weight, preferably in the range of 6 to 9% by weight, based on the total weight of the alloy. By increasing the content of Sn to not less than 5% by weight based on the total weight of the alloy, the improvement in contrast and opaqueness to X-ray can be recognized. If the content of Sn exceeds 10% by weight, however, the excess would be at a disadvantage in degrading the produced alloy in corrosion resistance and cold workability and in workable reduction ratio as well.

Alternatively, in the fourth aspect of this invention, Nb and/or Ta as the component elements of the Ti—Zr type alloy may be substituted by at least one second subtituent element selected from the group consisting of Pd, Pt, and Au. In this case, the content of the at least one second subtituent element may be decided depending on the kind of the second subtituent element and the content of the substituted Nb and/or Ta. All these second subtituent elements excel in corrosion resistance. By having Nb and/or Ta substituted by these elements, the corrosion resistance of the mother material can be improved. Moreover, since these second subtituent elements have no adverse effects on a biological tissue and excel in affinity with a biological tissue, the alloy proves particularly suitable for the use in a medical appliance of this invention.

The composition of the alloy according to the present aspect does not need to be particularly discriminated but is required only to satisfy the conditions of the composition mentioned above. As typical examples of the composition, the following compositions may be cited.

a) A multi-element alloy of a composition, $Ti_{a1'} Zr_{b1'} Nb_{c1'}$ (at least one second subtituent element selected from the group consisting of Pd, Pt, and Au)$_{d1'}$ (wherein a1' stands for the content of Ti (% by weight) falling in the range of 25 to 50, b1' for the content of Zr (% by weight) falling in the range of 25 to 60, c1' for the content of Nb (% by weight) falling in the range of 5 to 30, and d1' for the total content of the second subtituent element (% by weight) falling in the range of 5 to 40, provided that the ratio, b1'/a1', fall in the range of 0.5 to 1.5 and the ratio, c1'/d1', in the range of 0.125 to 1.5);

b) A multi-element alloy of a composition, $Ti_{a2'} Zr_{b2'}$ (at least one second subtituent element selected from the group consisting of Pd, Pt, and Au)$_{c2'} Ta_{d2'}$ (wherein a2' stands for the content of Ta (% by weight) falling in the range of 25 to 50, b2' for the content of Zr (% by weight) falling in the range of 25 to 60, c2' for the total content of the second subtituent element (% by weight) falling in the range of 5 to 30, and d2' for the content of Ta (% by weight) falling in the range of 5 to 40, provided that the ratio, b2'/a2', fall in the range of 0.5 to 1.5 and the ratio, c2'/d2', in the range of 0.125 to 1.5); and c) A multi-element alloy of a composition, $Ti_{c3}$, $Zr_{b3'}$(at least one second subtituent element selected from the group consisting of Pd, Pt, and Au)$_{c3'+d3'}$ (wherein a3' stands for the content of Ti (% by weight) falling in the range of 25 to 60, b3' for the content of Zr (% by weight) falling in the range of 25 to 60, and c3'+d3' for the total content of the second subtituent elements (% by weight) falling in the range of 10 to 50, provided that the ratio, b3'/a3', fall in the range of 0.5 to 1.5).

In this invention, the second subtituent elements may be suitably selected, depending on the intended use and the required quality, in due consideration of the properties as mentioned above, as follows.

Alternatively, in this invention, the Ti—Zr type alloy mentioned above may incorporate therein at least one second additive element selected from the group consisting of Pd, Pt, and Au in an amount in the range of 0.01 to 5% by weight, based on the total weight of the component elements of the alloy. All the second additive elements, Pt, Au, and Pd, are elements excellent in corrosion resistance. By having the alloy incorporate therein the second additive element in the specified proportion, the mechanical strength and corrosion resistance of the mother material can be improved. Further, these additive elements have no adverse effects on a biological tissue and excel in affinity with a biological tissue, the alloy is suitable for the use in a medical appliance of this invention.

When the second additive element is to be used, the content of this second additive element is preferably in the range of 0.01 to 5% by weight, more preferably in the range of 1 to 4% by weight, and most preferably in the range of 2 to 3% by weight, based on the total weight of the component elements of the alloy. In this case, if the content of the second additive element is less than 0.01% by weight, the shortage would be at a disadvantage in preventing effects obtained by adding the second additive element from being manifested appreciably and suffering the added element to function like the extraneous trace element. Conversely, if the content of the second additive element exceeds 5% by weight, the excess would be at a disadvantage in causing the produced alloy to manifest a quality different from the expected quality.

The method for producing the Ti—Zr type alloy according to the fourth aspect of this invention does not need to be particularly discriminated but is required only to be capable of producing an alloy having such a specific composition as mentioned above. As typical examples of this method of production, a method which comprises steps of weighing required elements (for example, Ti in the form of sponge titanium and pure titanium, Grades 1 to 4; Zr in the form of sponge zirconium and pure zirconium; Nb in the form of pure niobium; and Ta in the form of pure tantalum, each possessing no specifically limited shape and having purity enough to avoid exerting adverse effects on the quality of the produced alloy) in a prescribed composition (% by weight), arc melting the elements in a water-cooled copper hearth, transforming the resultant molten mass into an alloy, and forming the alloy in an ingot; a method which comprises steps of melting the elements in a crucible, transforming the molten mass into an alloy, and atomizing the alloy into a powder; a method which comprises steps of similarly melting the elements and casting the resultant molten mass; a method which comprises steps of levitation melting the elements, transforming the molten mass into an alloy, and forming the alloy in an ingot; such methods as a mechanical alloying method, a sputtering method, and a plasma method which have been generally carried out on a commercial scale; and methods published by various research institutes and reported in literature may be cited. When Sn, the second substituent element, or the second additive element is to be used, the form of the element does not need to be particularly limited but may be the same as in any of known methods. It may be used in the form of pure metal, for example.

The Ti—Zr type quaternary alloy according to the fourth aspect which has a composition in the specified range mentioned above can exhibit exceptionally fine workability such that the work of rolling, forging, or mechanical processing can be carried out at normal temperature in spite of the fact that it is an alloy having Ti and Zr as main components thereof because the metallic texture thereof assumes the β-phase at normal temperature without requiring any special heat-treatment. The medical appliance having a part formed of this Ti—Zr type alloy, therefore, can be easily rolled, cast, or mechanically processd even when they have complicated shape and construction.

Since this invention is characterized by using a novel Ti—Zr type alloy which excels conventional Ti-based alloy in terms of biocompatibility, workability, and physical properties, all the conventional medical appliances which are intended for biological materials can be similarly applied as the medical appliance of this invention having a part formed of the Ti—Zr type alloy mentioned above. The medical appliances of this invention include artificial hearts, artificial valves, pacemakers, and etc. as disclosed in EP-A-601,804; artificial joints, bone screws, bone plates, and etc. as disclosed in EP-A-437,079; and guide wires, catheters, stents, stent grafts, venous filters, artificial blood vessels, ventricular assisting device, and dental implants. Among other medical appliances cited above, stents, guide wires, ventricular assisting devices, housings for pacemakers, particularly stents, guide wires, and ventricular assisting devices prove suitable.

According to the fifth aspect of this invention, therefore, a guide wire, a stent, and a ventricular assisting device which comprises a metallic functional body formed of the Ti—Zr type alloy according to the fourth aspect of this invention are provided.

According to the sixth aspect of this invention, a medical appliance destined to contact with blood, which comprises a functional body formed of the Ti—Zr type alloy according to the fourth aspect of this invention, and has heparin covalently bound to the surface of the alloy destined to contact with blood, preferably a guide wire, a stent, or a ventricular assisting device is provided. The invention of this aspect has been perfected based on the present inventors' knowledge that the alloy according to the fourth aspect of this invention can retain heparin by covalent binding thereon and imparting antithrombogenesity by virtue of the fact that the alloy copiously contains such easily oxidizing metals as Ti and Zr.

In the fifth aspect, the formation of the functional bodies for a guide wire, a stent, and a ventricular assisting device from the Ti—Zr type alloy may be attained by adopting any of methods known to the art. As typical examples of the method which is available for this purpose, wire drawing, drawing, etching, laser beam machining, casting, forging, press working, cutting, and metal injection molding (MIM) may be cited. The molded shape and structure can be adopted similar to known shape and structure.

In the sixth aspect, the binding of heparin on the surface of an alloy destined to contact with blood may be attained by using any of methods known to the art. A method which comprises oxidizing the alloy surface with ozone, immobilizing polyethylene imine through reaction on the oxide coat, and immobilizing heparin on the polyethylene imine layer through the medium of glutar aldehyde may be utilized. By immobilizing heparin on the alloy surface as described above, a highly desired properties can be imparted to a medical appliance destined to contact directly with blood. Instead of the bnding of heparin, a medical appliance of this invention may be given by any of such anti-thrombogenic treatments as coating with diamond-like carbon (DLC), a material in popular use, coating with Parelyn by a chemical vapor deposition technique, and surface lubrication with tetrafluorochloride resin (Teflon) or esters. These treatments may be carried out in combination with nearly all existing coating techniques. In addition, methods for coating the alloy surfaces with compositions containing agents may be arbitrarily selected, depending on the kind of medical appliance. For example, the outer surfaces of the medical appliance formed of the Ti—Zr type alloy of this invention may be hardened or modified by such treatments as hardening by oxygen diffusion, hardening with nitrogen, physical vapor deposition, chemical vapor deposition, ion injection, and doping.

Now, the embodiments of the medical appliances of this invention will be specifically described below with reference to the drawings. Table 1 shows the comparison between the examples of compositions of alloys to be used in this invention and examples of compositions of the conventional alloys. It is noted from Table 1 that the compositions of the alloys of this invention are novel compositions characterized by containing Ti and Zr in substantially equal amounts and containing Zr in a relatively large amount as compared with those of the conventional alloys.

TABLE 1

| Example of Alloy | Composition of Alloy | Composition (% by weight) | | | | | | | | |
|---|---|---|---|---|---|---|---|---|---|---|
| | | Ti | Zr | Nb | Ta | Au | Sn | Pd | Al | V |
| Example-1 of alloy of this invention | Ti-34.8Zr-11.8Nb-23.0Ta | 30.4 | 34.8 | 11.8 | 23 | 0 | 0 | 0 | 0 | 0 |
| Example-2 of alloy of this invention | Ti-29.8Zr-12.1Nb-23.6Ta | 34.4 | 29.8 | 12.1 | 23.6 | 0 | 0 | 0 | 0 | 0 |
| Example-3 of alloy of this invention | Ti-24.5Zr-12.5Nb-24.3Ta | 38.7 | 24.5 | 12.5 | 24.3 | 0 | 0 | 0 | 0 | 0 |
| Example-4 of alloy of this invention | Ti-34.4Zr-11.7Nb-22.7Ta-1.2Au | 26.9 | 30.7 | 10.4 | 20.3 | 11.6 | 0 | 0 | 0 | 0 |
| Example-5 of alloy of this invention | Ti-36.2Zr-12.3Nb-12.0Ta-7.9Sn | 31.6 | 36.2 | 12.3 | 12 | 0.0 | 7.9 | 0 | 0 | 0 |
| Control-1 of alloy | Ti-13Zr-13Nb | 74 | 13 | 13 | 0 | 0 | 0 | 0 | 0 | 0 |
| Control-2 of alloy | Ti-15Zr-4Nb-4Ta-0.2Pd | 76.8 | 15 | 4 | 4 | 0 | 0 | 0.2 | 0 | 0 |
| Control-3 of alloy | Ti-29.2Nb-12.4Ta-7.1Zr | 51.3 | 7.1 | 29.2 | 12.4 | 0 | 0 | 0 | 0 | 0 |
| Control-4 of alloy | Ti-6Al-4V | 90 | 0 | 0 | 0 | 0 | 0 | 0 | 6 | 4 |
| Control-5 of alloy | Ti | 100 | 0 | 0 | 0 | 0 | 0 | 0 | 0 | 0 |
| Control-6 of alloy | Zr | 0 | 100 | 0 | 0 | 0 | 0 | 0 | 0 | 0 |
| Control-7 of alloy | JIS SUS316L | 0 | 0 | 0 | 0 | 0 | 0 | 0 | 0 | 0 |

Table 2 given below shows the results of a rolling test (for rating cold workability) at room temperature and the results of a test for contrast and opaqueness to X-ray on examples of the alloy of this invention manufactured as described above. In this case, the rolling test was performed by preparing a cast plates each of given alloys and examining whether the cast plate can be subjected to rolling at room temperature. The samples which could be cold rolled without sustaining a crack were marked with ○.

It is noted from Table 2 that the conventional Ti-based alloys are not easily subjected to such a mechanical workings as rolling, forging, or cutting because their metallic compositions assumed a rigid and brittle α-phase at normal temperature and that they can be processed only in the β-phase region separated in a high temperature range. It is well known that the Zr type alloys are difficult to be worked because the element Zr itself easily fires. It is a well-known fact that a Ti alloy and a Zr alloy are not easily subjected to mechanical working at room temperature because they tend to sustain a crack. The fact that the material for the use in this invention is cold workable, therefore, forms an epoch-making discovery in a sense that the popular mechanical working techniques can be applied to an alloy used in vivo.

For the contrast and opaqueness to X-ray under X-ray fluoroscopy indicated in Table 2 shown below, the test was carried out by casting a given alloy to prepare a plate and buffing the plate with an abrasive used in combination with a waterproof paper until a prescribed thickness of 80 microns was obtained. The test for the contrast and opaqueness to X-ray was performed according to the method described in ASTM F640-79, with a given sample mounted on an Al shielding plate of 15 mm in thickness. The apparatus used for this test was a X-ray equipment (produced by Hitachi under the product name of "DHF-158CX") actually installed in a hospital. The X-ray image obtained by the equipment was read into a personal computer through via a scanner and the shadow displayed on the computer was converted into numbers. The numbers were obtained by expressing the shadow density as a gray scale, wherein the recognition of the X-ray image improved in proportion to the increase of the numbers, i.e., the darkness of the shade. To make the meaning of number expressed more sensibly, the number obtained of a given alloy plate of 80 microns in thickness under test was converted to thickness in microns of a gold plate by using a calibration curve of the gold plate of several thickness.

TABLE 2

| Example of Alloy | Composition of Alloy | Contrast and opaqueness t = 80, reduced to as thickness of gold (micron) | Cold workability | |
|---|---|---|---|---|
| | | | Rolling | Adaptability |
| Example-1 of alloy of this invention | Ti-34.8Zr-11.8Nb-23.0Ta | 20.6 | ○ | Adaptable |
| Example-2 of alloy of this invention | Ti-29.8Zr-12.1Nb-23.6Ta | 20.5 | ○ | Adaptable |
| Example-3 of alloy of this invention | Ti-24.5Zr-12.5Nb-24.3Ta | 20.3 | ○ | Adaptable |
| Example-4 of alloy of this invention | Ti-34.4Zr-11.7Nb-22.7Ta-1.2Au | 28.4 | ○ | Adaptable |
| Example-5 of alloy of this invention | Ti-36.2Zr-12.3Nb-12.0Ta-7.9Sn | 23.8 | ○ | Adaptable |
| Control-1 of alloy | Ti-13Zr-13Nb | 11.9 | x | Crack |
| Control-2 of alloy | Ti-15Zr-4Nb-4Ta-0.2Pd | 16.1 | x | Crack |
| Control-3 of alloy | Ti-29.2Nb-12.4Ta-7.1Zr | 19.4 | x | Crack |
| Control-4 of alloy | Ti-6Al-4V | 2.7 | x | Crack |
| Control-5 of alloy | Ti | 3.2 | x | Crack |
| Control-6 of alloy | Zr | 24.4 | x | Crack |

TABLE 2-continued

| Example of Alloy | Composition of Alloy | Contrast and opaqueness t = 80, reduced to as thickness of gold (micron) | Cold workability Rolling | Adaptability |
|---|---|---|---|---|
| Control-7 of alloy | JIS SUS316L | 8.2 | ○ | Adaptable |
| Living bone | Backbone | 20.0 | — | — |
| Living bone | Rib | 12.2 | — | — |

Figure 2:
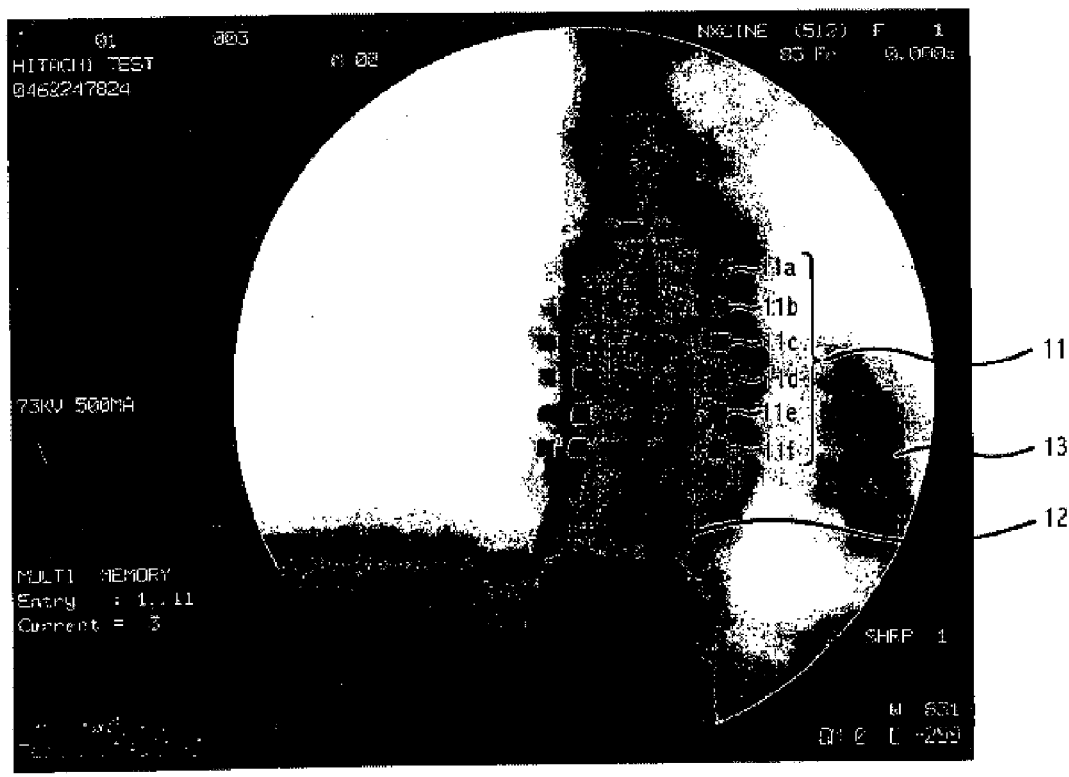
FIG. 2 is an X-ray image of pure gold to be photographed under the photographic condition of the examination of the coronary artery, namely a photograph for aiding in the explanation of the X-ray contrast and opaqueness expressed in numerical value.
Figure 3:
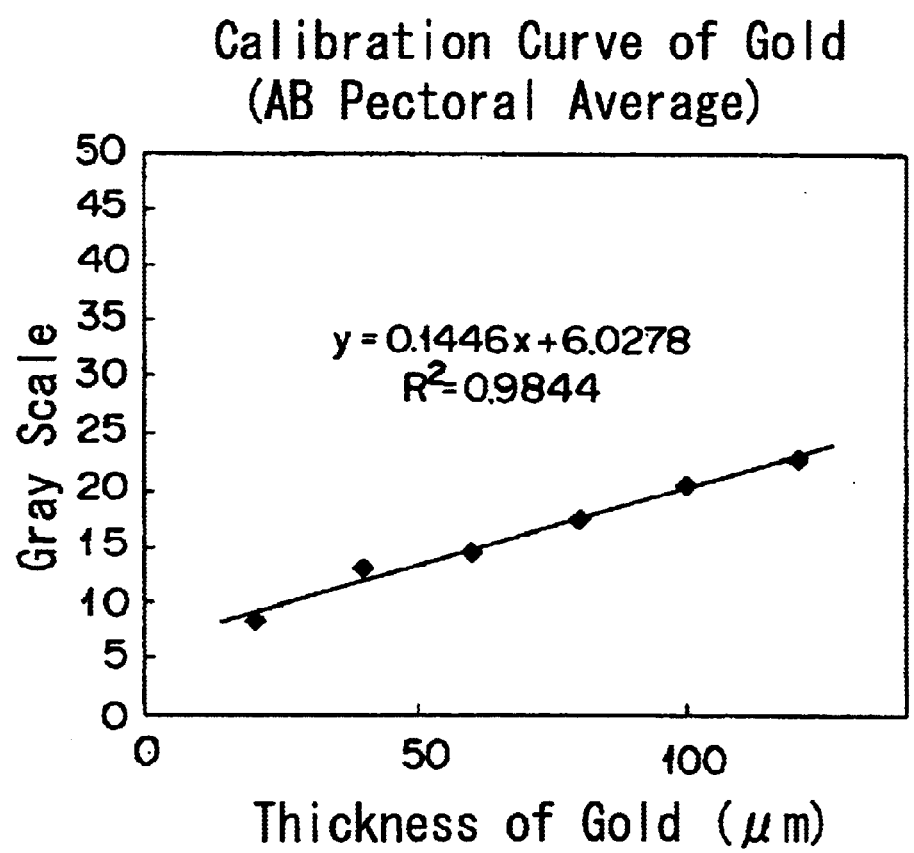
FIG. 3 is a diagram of a calibration curve for X-ray contrast and opaqueness of pure gold obtained by image processing the data of FIG. 2 using a personal computer.

Further, for the purpose of converting X-ray contrast and opaqueness at an actual medical site into a numerical value, pure gold plates of various thickness in the range of 20 to 120 microns to be used for the preparation of a calibration curve were placed on a human body under X-ray conditions (73 kV/500 mA) which have been generally adopted in the test with contrast medium for coronary artery (CAG: coronary angiography), as shown in FIG. 2. FIG. 2 shows an X-ray image for the preparation of a calibration curve using pure gold plates 11, measuring the square of 5 mm in size and 20, 40, 60, 80, 100, and 120 microns (respectively corresponding to the reference numerals, 11a–11f, on the image) in thickness, to be arranged in the order of thickness in such a manner that the row of calibration curve may be positioned directly above the heart. The X-ray was radiated from the back side to allow observation of the backbone 12 and the ribs 13. The calibration curve obtained at this time is illustrated in FIG. 3. From the graph shown therein, it is noted that the thickness of gold plates and the numerical value on the gray scale show a fine correlation. Though it is inferred from FIG. 3 that the X-ray contrast and opaqueness satisfied additivity of the gray scale to a certain extent, the calibration curve failed to pass the origin because the a background noise was difficult to be removed in the case of a human body. In other words, when the thickness of a gold plate decreased below 10 microns, the gold plate became invisible because the contrast between the gold plate and bone nearly disappeared and became substantially indistinguishable. As a result, it was found necessary to perform the pertinent measurement of samples and convert the data into numerical values simultaneously with the preparation of a calibration curve using gold plates. Incidentally, in FIG. 2, the opaqueness of the backbone 12 of human was found to correspond to a thickness of 20 microns of a gold plate and the ribs 13 to a thickness of about 12 microns of a gold plate on the X-ray image.

Figure 4:
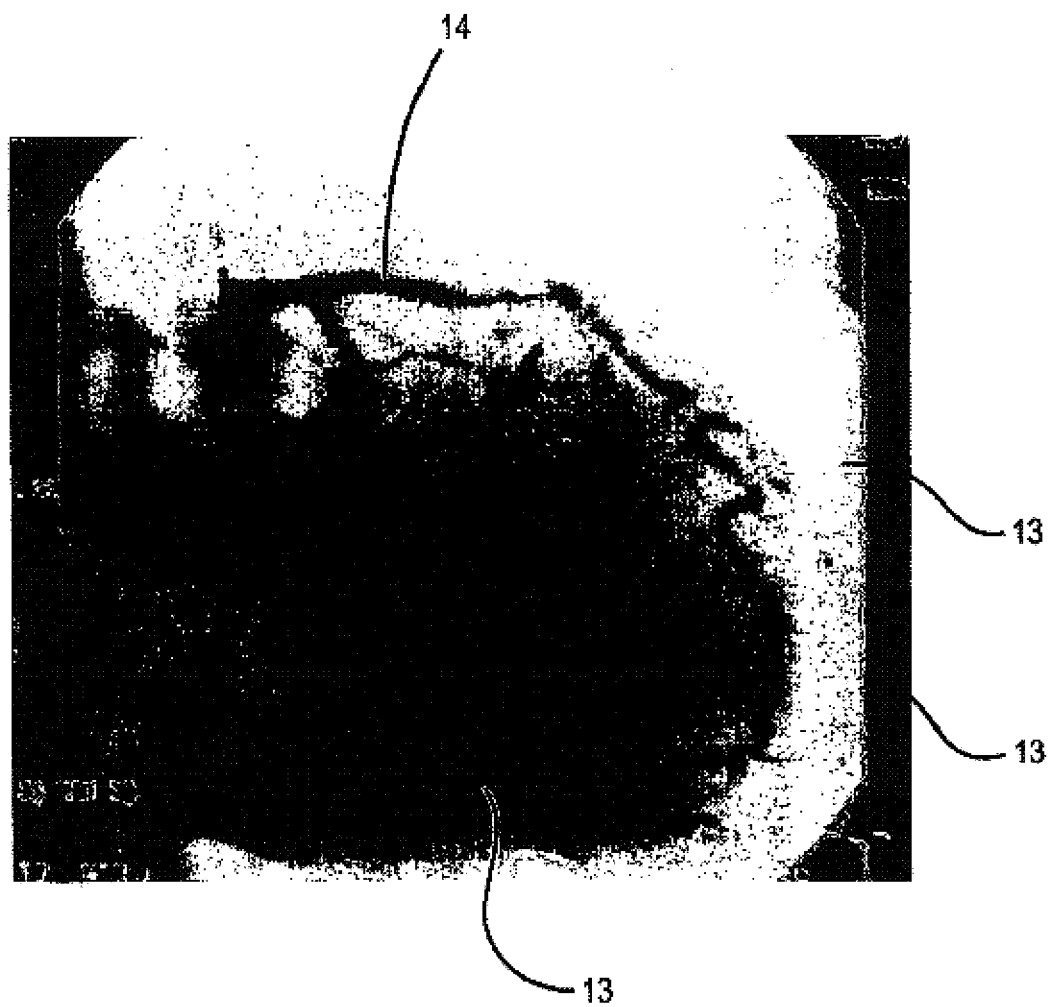
FIG. 4 is an X-ray image of the left coronary artery photographed during the X-ray examination of a human coronary artery, the image depicting a blood vessel made visible with a liquid contrast medium injected into a vessel, i.e., a photograph for aiding in the explanation of the X-ray contrast and opaqueness of the contrast medium in numerical value.

In angiography, a given blood vessel is made visible by injecting a contrast medium via a catheter into the blood vessel. Actually, the blood vessel is observed as shown in FIG. 4. From this image, it is found that an injected liquid contrast medium manifested X-ray opaqueness equivalent to 50 microns in average at a left coronary artery #6 site, namely, in the neighborhood of the point 14 in the diagram of FIG. 4, using the calibration curve of FIG. 3, though variable in darkness with locations. That is, the 50 micron thickness of a gold plate is a standard image level used by physicians in their daily diagnosis, and may well be called the clearly discernible level of contrast and opaqueness. In contrast, a commercial guide wire for contrastradiography (0.035 inch) corresponds to a thickness of 33 microns of gold. The guide wire for contrastradiography is rated by physicians and radiographers as excelling in visibility. The visibility under the X-ray fluoroscopy proves satisfactory when it is on a par with a commercially available thick guide wire for angiography (0.035 inch in outer diameter). This X-ray opaqueness may be regarded as one target magnitude. Actually, it has been found that X-ray opaqueness equivalent to a thickness of 20 microns of gold may be safely adopted as the target value because a gold plate 11a having a thickness of 20 microns can be distinguished from a backbone 13 and ribs 13, and the backbone 12, even when suffered to overlap with the ribs 13, can be distinguished from each other. From the results of the present experiment for X-ray contrast and opaqueness, it has been found that the lowest level of X-ray contrast and opaqueness is approximately a thickness of 10 microns of gold. It is further noted from the image of the samples 11d, 11e, and 11f that gold plates of a thickness exceeding 80 microns are not necessary. It may be concluded that when X-ray contrast and opaqueness is expressed in numerical value as reduced to as a thickness of gold, the contrast and opaqueness between 12 microns of the ribs and 50 microns of a given contrast medium constitutes an adequate X-ray contrast and opaqueness, and more preferably a thickness in the range of 20 to 40 microns of gold constitutes an adequate X-ray contrast and opaqueness. Specifically, the fact that when the total thickness of a sample is set to be in the range of 80 to 100 microns, the X-ray contrast and opaqueness of this sample is equivalent to a thickness in the range of 20 to 40 microns of a pure gold plate may be taken as a target. As concerns this point, it is noted from Table 2 given above that the Ti—Zr type alloy of this invention satisfies this condition fully satisfactorily. It has been also found that the contrast and opaqueness can be controlled by the contents of Ta, Sn, etc. as demonstrated by the data of Example 5 of alloy of this invention indicated in the above Tables 1 and 2. In this invention, since the X-ray contrast and opaqueness of a sample depends on the thickness thereof, a medical appliance having a proper contrast and opaqueness can be provided by setting such factors as thickness and mechanical strength in the course of designing a product and adjusting an alloy composition thereby controlling contrast and opaqueness of the product appropriately. As demonstrated by Example 4 of alloy of this invention indicated in Tables 1 and 2, the contrast and opaqueness of the alloy can be controlled by incorporating in the alloy a noble metal (Au) as a second additive element. Though the Ti alloy modified with a high Nb alloy or simple element of Zr is embraced in the scope of this invention, it lacks practicability because it is incapable of cold working and inferior in workability.

Figure 6:
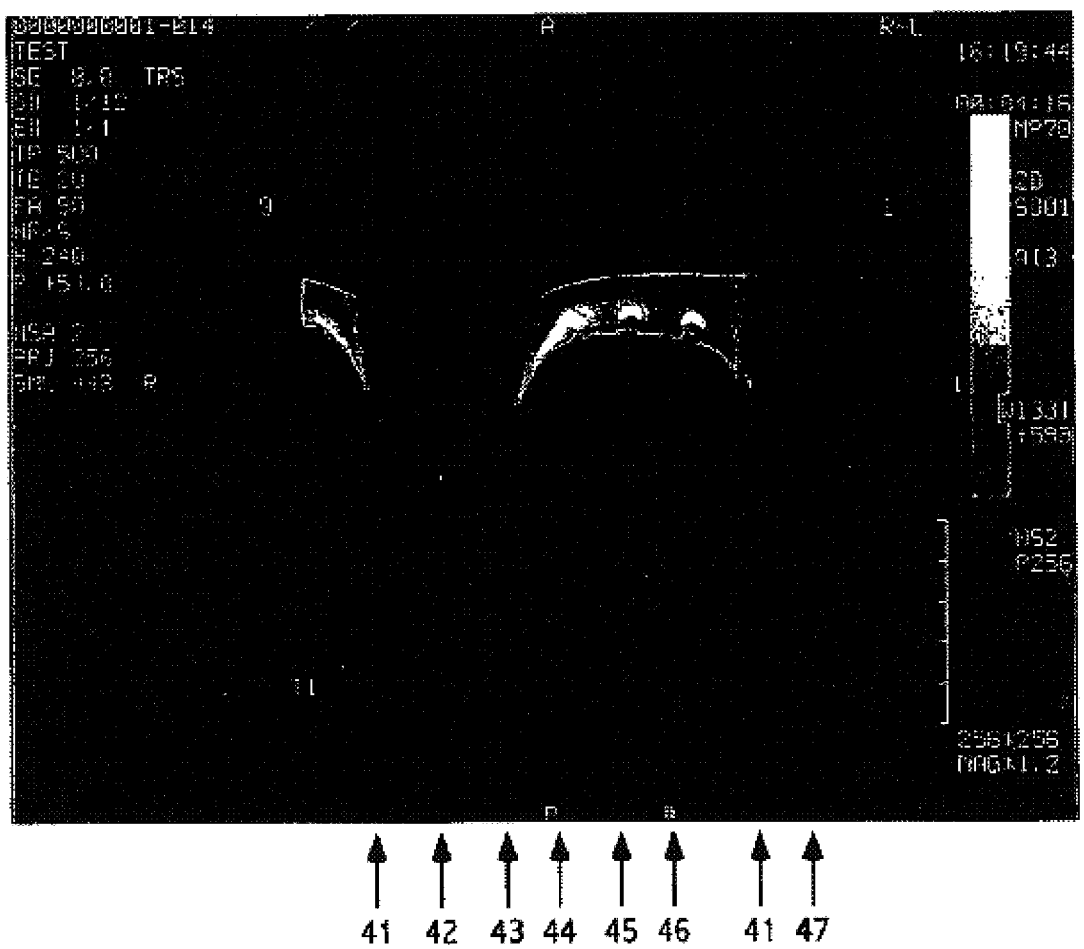
FIG. 6 is a MR image of the sample laid out as illustrated in FIG. 5, the image taken in a section perpendicular to the longitudinal direction of the sample.

Table 3 given below further shows the results of the tensile test, the results of the bending test, and the measurement results of the hardness performed on examples of the alloy of this invention to obtain mechanical properties. The data of tensile strength, Young's modulus, and hardness shown in Table 3 were obtained by the same procedures as described in Example 1 below. As regards the results of the bending test, since the test was performed solely for a plate which could be rolled at normal temperature and sustained no crack, the results exclude those of the examples of the alloys of conventional technique which could not withstand the test. From the numerical data offered by literature and disclosed in patent publications, it is known that the tensile strength of a conventional Ti alloy is lower than 1000 Mpa and that of stainless steel (JIS SUS316L), is about 940 Mpa. From these facts, it is observed that the Ti—Zr type alloy of this invention has higher tensile strength and proves advantageous for product design.

showing cross sections of wire samples perpendicular against the direction of length thereof (FIG. 6) and the MR image showing the cross sections of the samples parallel to the direction of length thereof (FIG. 7) were obtained. FIG. 6 is a typical image of the longitudinal cross section. It is noted from this image that the SUS304 of the reference number 42 and the SUS631 of the reference number 47 produce very large artifacts in spite of the heretofore per-

TABLE 3

| Example of Alloy | Composition | Density $\rho$ (g/cm) | Tensile strength $\sigma f$ (MPa) | Young's modulus E (GPa) | Hardness (Hv) Vicker's | 3-point bending strength $\sigma b$ (MPa) |
|---|---|---|---|---|---|---|
| Example-1 of alloy of this invention | Ti-34.8Zr-11.8Nb-23.0Ta | 6.7 | 1070 | 55 | 350 | 2600 |
| Example-2 of alloy of this invention | Ti-29.8Zr-12.1Nb-23.6Ta | 6.63 | 985 | 60.5 | 365 | 2530 |
| Example-3 of alloy of this invention | Ti-24.5Zr-12.5Nb-24.3Ta | 6.55 | 1000 | 58 | 370 | 2550 |
| Example-4 of alloy of this invention | Ti-34.4Zr-11.7Nb-22.7Ta-1.2Au | 6.78 | 1500 | 65.2 | 420 | 2500 |
| Example-5 of alloy of this invention | Ti-36.2Zr-12.3Nb-12.0Ta-7.9Sn | 6.1 | 1100 | 55 | 350 | 2530 |

The Ti—Zr type alloy of this invention, in the form of a plate having a thickness of 80 microns, manifests an X-ray contrast and opaqueness equivalent to a gold plate of not less than 20 microns in thickness, can be distinguished from ribs and backbone, and is less opaque than a contrast medium and thus can be distinguished therefrom. Accordingly, this alloy has been found to have a proper contrast and opaqueness. It has been also found to excel conventional materials in workability and mechanical strength. Since this property is important for a stent for the use in a blood vessel and a micro guide wire, it will be described more specifically with reference to the following working examples.

Figure 5:
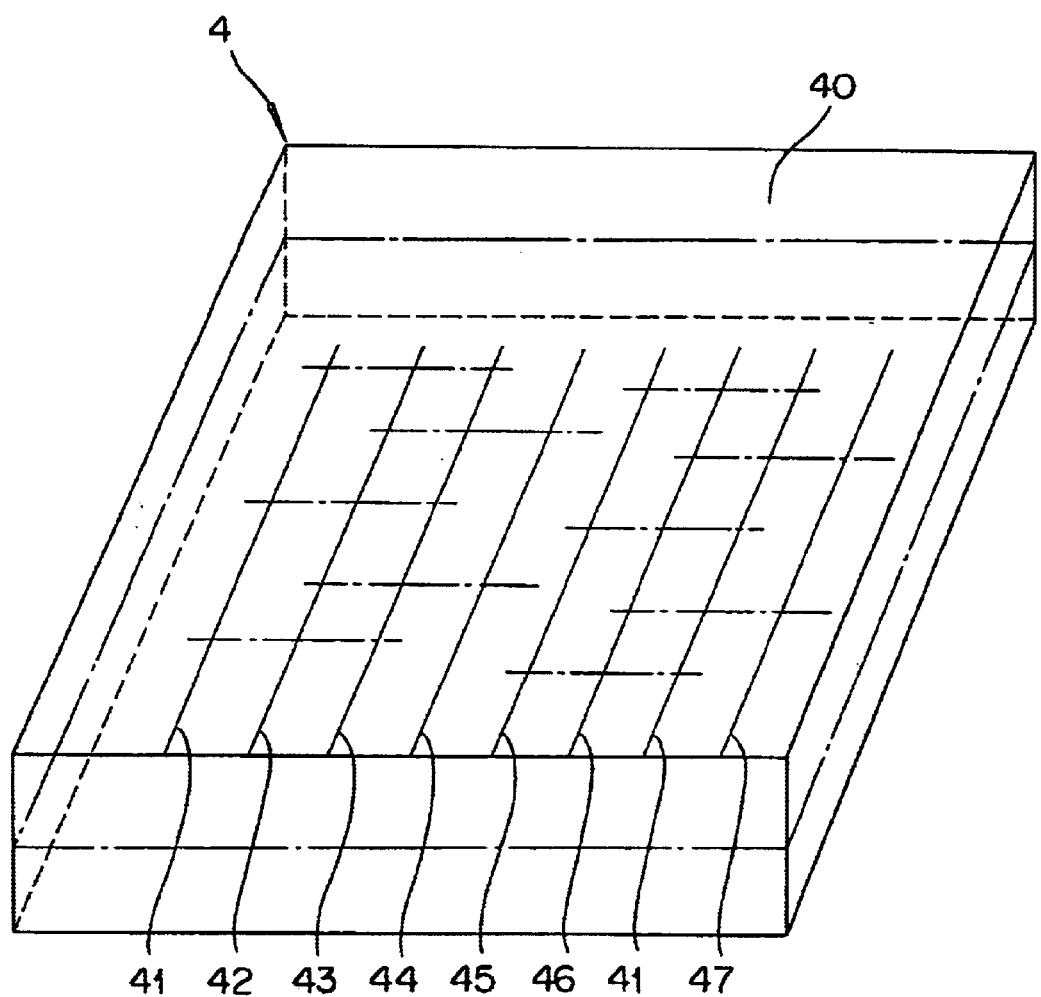
FIG. 5 is a perspective view for illustrating the arrangement of alloy samples of this invention to be tested during the photographing of the MR image of the tested samples.
Figure 7:
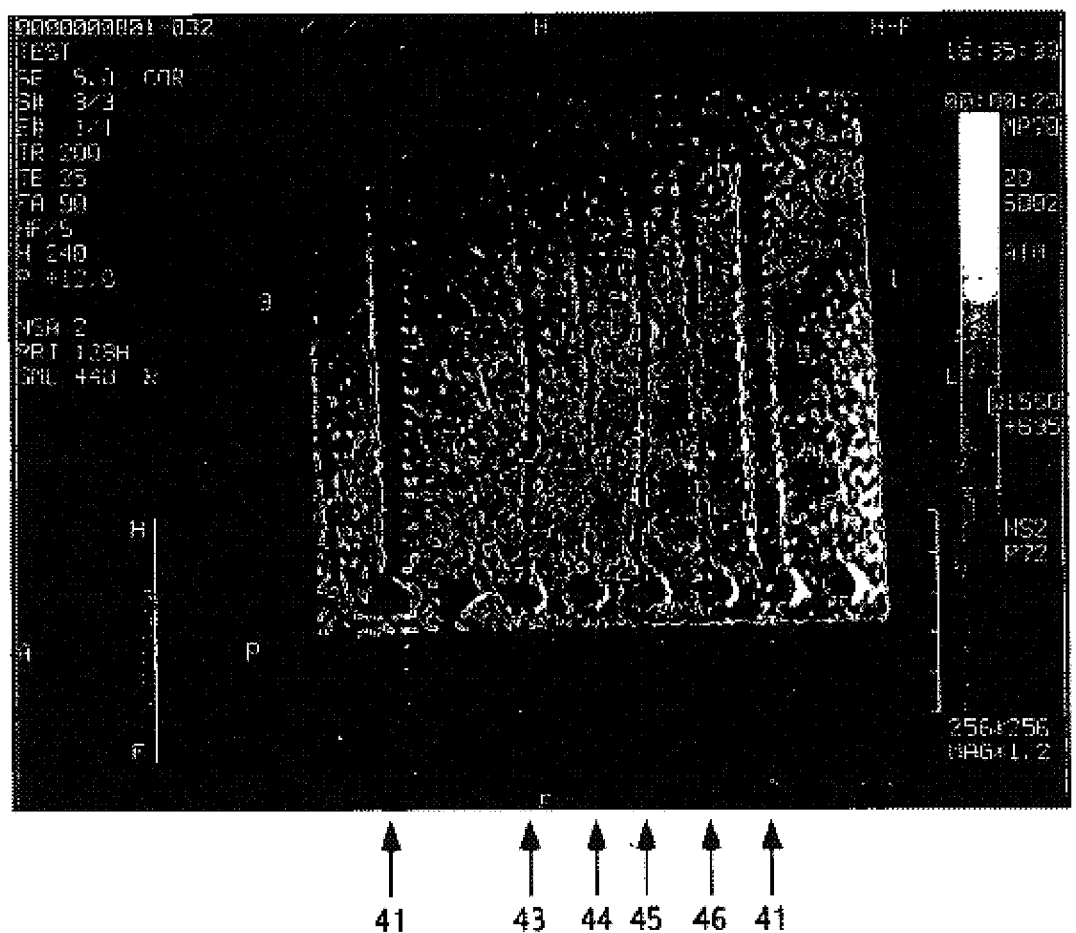
FIG. 7 is a MR image of the sample laid out as illustrated in FIG. 5, the image taken in a section parallel to the longitudinal direction of the sample.

FIG. 6 and FIG. 7 are images obtained by a magnetic resonance imaging diagnostic device (in the present specification, occasionally referred to simply as "MRI") of the alloy of this invention molded in the form of a wire of 0.5 mm in diameter. FIG. 5 is a perspective view showing the arrangement of samples, portraying the appearance of wires of 0.5 mm in diameter and 6 cm in length to be placed in order in a vat filled with physiological saline. In FIGS. 5 to 7, the reference numeral 4 denotes a plastic vessel and the reference numeral 40 a physiological saline. The reference numerals 41–47 represent metallic wires as samples. The reference numeral 41 represents a commercially available stainless steel (JIS SUS316L) material (hereinafter referred to briefly as "SUS316L"), the reference numeral 42 a commercially available stainless steel (JIS SUS304) material (hereinafter referred to as "SUS304"), the reference numeral 43 a commercially available $\alpha+\beta$ titanium, Ti-6Al-4V material (hereinafter referred to briefly as "64Ti"), the reference numeral 44 a Ti—Zr alloy wire manufactured from Example-1 of alloy of this invention, Ti-34.8Zr-11.8Nb-23.0Ta alloy (composition is expressed as "% by weight") (hereinafter referred to briefly as "Ti—Zr alloy"), the reference numeral 45 a commercially available JIS Type 2 pure Ti wire (hereinafter referred to briefly as "Ti"), reference numeral 46 a commercially available Ni—Ti superelastic wire (hereinafter referred to briefly as "Ni—Ti"), and the reference numeral 47 a stainless steel (JIS SUS631) material (hereinafter referred to briefly as "SUS631"). By the use of an actual device, Hitachi MRP7000 (magnetic field strength: 0.3 tesla), the MR image sisting anxiety. The wires of 0.5 mm in diameter are magnified like a bar and consequently suffered to exert an influence on the image of diagnosis. In FIG. 6, the image of the 316L of the reference numeral 41 is observed to form a streak and the image of the 64Ti of the reference numeral 43 is observed to render location thereof no longer possible under the influence of a large artifact of the SUS304 of the reference numeral 42. In contrast, the Ti type wires of the reference numerals 44, 45, and 46 are observed to exert virtually no influence on images and consequently produce images of nearly the same magnification. Since the observation of the cross section of FIG. 6 revealed that the SUS304 of the reference numeral 42 and the SUS631 of the reference numeral 47 were samples having unduly large artifacts, the transverse sections for the samples other than these two samples were observed. The results of the observation are shown in FIG. 7. The SUS316L of the reference numeral 41 has been known as a material producing a slight artifact on the image of the MR observation. By comparison with the SUS316L of the reference numeral 41, the Ti—Zr alloy wire of the reference numeral 44 as an example of alloy of this invention is found to produce no artifacts and allow MRI observation. The fact indicates that this alloy is on a par with the $\beta$-Ti alloy, 64 Ti wire of the reference numeral 43, the Ni—Ti wire of the reference numeral 46, and the pure Ti wire of the reference numeral 45. It has been already known to the art that the Ni—Ti superelastic alloy of the reference numeral 46 and the pure Ti of the reference numeral 45 produce no artifacts under MRI.

Figure 8:
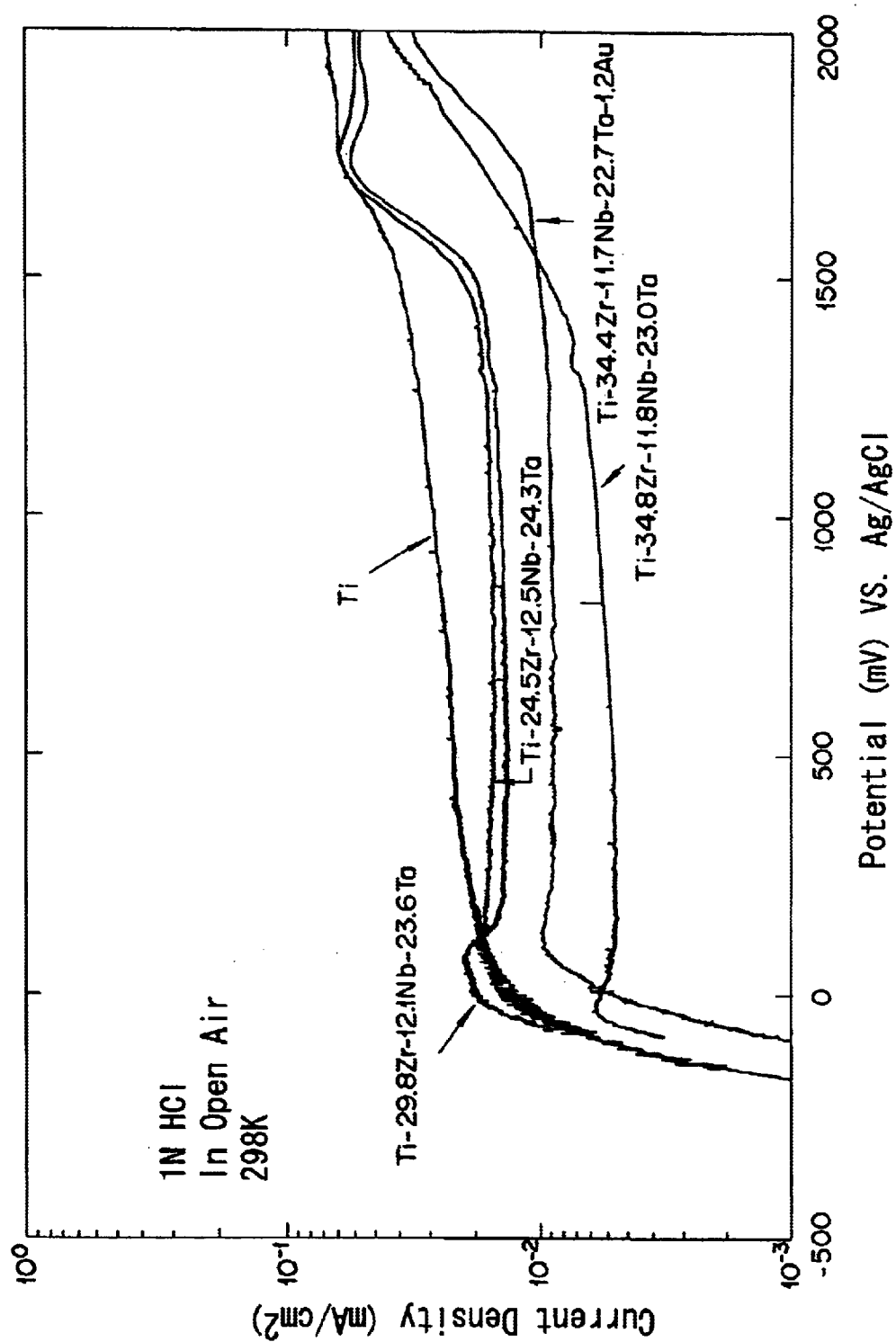
FIG. 8 is a characteristic diagram illustrating the results of an anodic polarization test performed on the sample alloys of this invention (Alloys #1 to 4 of this invention as shown in Table 1).

Further, FIG. 8 shows the results of an anodic polarization test performed on the Ti—Zr type alloys (Examples 1 to 4 of alloy of this invention) used in this invention in an 1N hydrochloric acid as compared with those of pure Ti samples (in detail, see Example 6). This test assumed retention of a sample in a stomach and was performed so as to determine whether or not alloys and pure Ti were corroded under extremely harsh conditions such as of gastric acid. It has been already known that pure Ti (JIS Type 2) excels such $\alpha+\beta$-Ti alloys as stainless steel (JIS SUS316L), a cobalt alloy for the use in vivo, and a Ti-6Al-4V (ELI) alloy in corrosion resistance. The Ti type alloy used in this invention exhibits still a lower current value than the pure Ti and may well be rated as remarkably excellent in corrosion resistance. That is, the Ti type alloy used in this invention can be regarded as an alloy having the highest level of corrosion resistance and proves suitable as a material used in vivo.

As described above, the Ti type alloy according to this invention should be fully understood to be a novel Ti—Zr type alloy suitable as a material for a medical appliance and as a material used in vivo. The examples of the applications of this alloy in more detail will be described with reference to the following working examples. This invention is characterized by using a novel Ti—Zr type alloy which excels conventional Ti alloys in terms of biocompatibility, workability, and physical properties. It can be applied to all the medical appliances that contemplate utilizing conventional materials used in vivo. As typical examples of such medical appliances of this invention, artificial hearts, artificial valves, pacemakers, and etc. as disclosed in EP-A-601, 804; artificial joints, bone screws, bone plates, and etc. as disclosed in EP-A-437,079; and guide wires, catheters, stents, stent grafts, venous filters, artificial blood vessels, ventricular assisting device, and dental implants may be cited. Among other medical appliances cited above, stents, guide wires, ventricular assisting devices, housings for pacemakers, particularly stents, guide wires, and ventricular assisting devices prove suitable.

Now, this invention will be described more specifically below with reference to working examples. It should be noted, however, that this invention is not limited to the following working examples.

EXAMPLES 1 TO 4 AND CONTROLS 1 TO 7

Spong titanium, sponge zirconium, pure niobium, and pure tantalum were weighed out in amounts calculated to form the proportions shown in Table 4 given below and arc melted in a water-cooled copper hearth. The resultant melts were each converted into an alloy and then formed in ingots. The alloy formed in this process was not subjected to any specific heat-treatment.

These alloys were tested for the following mechanical properties and were respectively estimated as follows.

i) A tensile strength and a Young's modulus were determined by stretching a given test piece in accordance with JIS Z2201-1980 No. 6 at a strain rate of $1.67 \times 10^{-3} S^{-1}$ by the use of an Instron tensile tester.

ii) A hardness was determined by retaining a test piece under a test load of 50 g for 10 S and measuring an impression on the test piece as a Vickers' hardness by the use of a Micro-Vickers' hardness tester.

Table 4 shows mechanical properties of the alloys of Examples 1 to 4 of the present invention and those of the pure Ti and typical Ti alloys as controls. In Table 4, the contents of the component elements are expressed in "% by weight".

The X-ray diffraction diagram showing the β-phase of the Ti—Zr type quaternary alloy manufactured in Example 2 is shown in FIG. 1.

TABLE 4

|  | Density ρ (g/cm) | Tensile strength of (MPa) | Young's modulus E (GPa) | Hardness (Hv) |
| --- | --- | --- | --- | --- |
| Example 1: Ti—27.42Zr—11.17Nb—32.63Ta | 7.204 | 1000 | 55.0 | 330 |
| Example 2: Ti—34.8Zr—11.8Nb—23.0Ta | 6.724 | 1070 | 55.0 | 350 |
| Example 3: Ti—29.8Zr—12.14Nb—23.64Ta | 6.636 | 985 | 60.5 | 365 |
| Example 4: Ti—24.5Zr—12.5Nb—24.3Ta | 6.546 | 1000 | 58.0 | 370 |
| Control 1: Pure Ti (Grade 2) | 4.540 | 345 | 106.0 | 170 |
| Control 2: Ti—6Al—4V | — | 895 | 110.0 | — |
| Control 3: Ti—13Nb—13Zr | — | 973 | 79.0 | — |
| Control 4: Ti—15Mo—5Zr—3Al | — | 852 | 80.0 | — |
| Control 5: Ti—29Nb—13Ta—4.6Zr | — | 911 | 80.0 | — |
| Control 6: Ti—14Zr—4Nb—4Ta—0.2Pd—0.2O—0.05N | — | 881 | 100.0 | 301 |
| Control 7: Ti—15Sn—4Nb—2Ta—0.2Pd—0.2O—0.005N | — | 966 | 86.0 | 336 |

As shown in Table 4 given above, the alloys obtained in Examples 1 to 4 are sturdy as evinced by the fact that they manifest a sufficiently low Young's modulus of not more than 70 Gpa as compared with the pure Ti or other alloys of the controls and they possess a tensile strength (Pa)/Young's modulus (Pa) ratio of not less than 0.016. At the same time, the alloys of this invention are most suitable particularly for heads, faces, and shafts in wood clubs and iron clubs for golf and also usable as industrial materials because they have enough tensile strength which is meant as stress manifested by a given sample when broken. Since these alloys show numerical values closely approximating to those of a living bone, they may well be rated as a material just ideal for the use in a medical appliance.

Then, the alloys of Examples 1 to 4 manifested excellent cold plastic workability as evinced by the fact that they invariably could be cold rolled till a reduction ratio of 98% with no ruptures nor cracks caused. In contrast, when the alloys of Controls 1 to 6 were tried to be cold rolled similarly, they invariably sustained ruptures and cracks during the course of rolling. Thus, the alloys of this invention, even for the use in the general industry, excel Ti-based alloys known to the art in cold plastic workability. They can be easily worked or molded, cold and hot alike, in expected shapes. They guide to a Ti-based alloy for the use as a material for general industry.

EXAMPLE 5

Sponge titanium, sponge zirconium, pure niobium, pure tantalum, and pure gold were weighed out in amounts calculated to form proportions shown in Tables 5-1 and 5-2 given below and then arc melted in a water-cooled copper hearth. The resultant melt was converted into an alloy and the alloy was formed in ingots.

Then, this alloy was rated for mechanical properties in the same manner as in Examples 1 to 4. The results are shown in Tables 5-1 and 5-2 given below.

The alloy of Example 5 was a product obtained by having Au as a first additive element incorporated in a quaternary alloy composed of Ti, Zr, Nb, and Ta. It veritably excelled in corrosion resistance. Since Au as the first additive element is a metal excellent in affinity with a biological tissue and harmless to human body, the produced alloy can be considered to excel in affinity with a biological tissue and do no harm to human body, and thus can be expected to be applied to a medical appliance.

TABLE 5-1

|  | Density ρ (g/cm) | Tensile strength σf (MPa) |
|---|---|---|
| Ti—34.35Zr—11.66Nb—22.71Ta—1.24Au | 6.780 | 1500 |

TABLE 5-2

|  | Young's modulus E (GPa) | Hardness (Hv) |
|---|---|---|
| Ti—34.35Zr—11.66Nb—22.71Ta—1.24Au | 65.5 | 420 |

EXAMPLE 6

The alloys obtained in Examples 2 to 4 and 5 and pure Ti of Control 1 were tested for electromotive potential anodic polarization in 1N hydrochloric acid held in open air using a glass electrolytic cell provided with a platinum wire as a counter electrode and an Ag/AgCl electrode as a reference electrode, a potentio/galvanostat, and a function generator to obtain the polarization curve and rate the corrosion resistance in the acid. In this example, the electrolytic cell was retained in a constant temperature water bath kept at 298 K. The results are shown in Table 8.

As clearly noted from FIG. 8, the alloys of this invention obtained in Examples 2 to 4 and 5 and the pure Ti were invariably in a passive state and the alloys of Examples 2 to 4 and 5 invariably manifested a lower passive current density than the pure Ti and had higher corrosion resistance than the pure Ti. The data indicate that the alloy of Example 2 showed the lowest passive current density and the highest corrosion resistance among all the alloys of Examples 2 to 4 and 5.

EXAMPLE 7

Sponge titanium, sponge zirconium, pure niobium, and pure tantalum were weighed out in amounts calculated to form proportions shown in Tables 6-1 and 6-2 given below and then arc melted in a water-cooled copper hearth. The resultant melt was converted into an alloy and the alloy was formed in ingots.

Then, this alloy was rated for mechanical properties in the same manner as in Examples 1 to 4. The results are shown in Tables 6-1 and 6-2 given below.

The alloy of Example 7 was obtained by having the content of Ta as one of the component elements of the quaternary alloy composed of Ti, Zr, Nb, and Ta relatively decreased. The alloy of Example 7 is suitable as a material for artificial bone material because it manifests sturdiness approximating most closely to a living bone. Further, it proves most suitable as a metallic alloy for medical treatment because it excels such typical known alloys, Ti-6Al-4V, Ti-13Nb-13Zr, and Ti-29Nb-13Ta-1.6Zr (see Table 4) currently attracting attentions as a metallic alloy for medical treatment in corrosion resistance and such mechanical properties as strength, Young's modulus, and hardness.

TABLE 6-1

|  | Density ρ (g/cm) | Tensile strength σf (MPa) |
|---|---|---|
| Ti—37.99Zr—12.90Nb—12.55Ta | 6.163 | 1348 |

TABLE 6-2

|  | Young's modulus E (GPa) | Hardness (HV) |
|---|---|---|
| Ti—37.99Zr—12.90Nb—12.55Ta | 62.0 | 400 |

EXAMPLE 8

Sponge titanium, sponge zirconium, pure niobium, and inorganic tin were weighed out in amounts calculated to form proportions shown in Tables 7-1 and 7-2 given below and arc melted in a water-cooled copper hearth. The resultant melt was converted into an alloy and the alloy was formed in ingots. The alloy of this example was obtained by having Sn as a first substituent element substituted for Ta in the component elements of the quaternary alloy composed of Ti, Zr, Nb, and Ta.

Then, the alloy was rated for mechanical properties in the same manner as in Examples 1 to 4. The results are shown in Tables 7-1 and 7-2 given below.

TABLE 7-1

|  | Density ρ (g/cm) | Tensile strength σf (MPa) |
|---|---|---|
| Ti—39.70Zr—13.48Nb—8.61Sn | 5.764 | 930 |

TABLE 7-2

|  | Young's modulus E (GPa) | Hardness (Hv) |
|---|---|---|
| Ti—39.70Zr—13.48Nb—8.61Sn | 53.0 | 390 |

EXAMPLE 9

Stent

Figure 9:
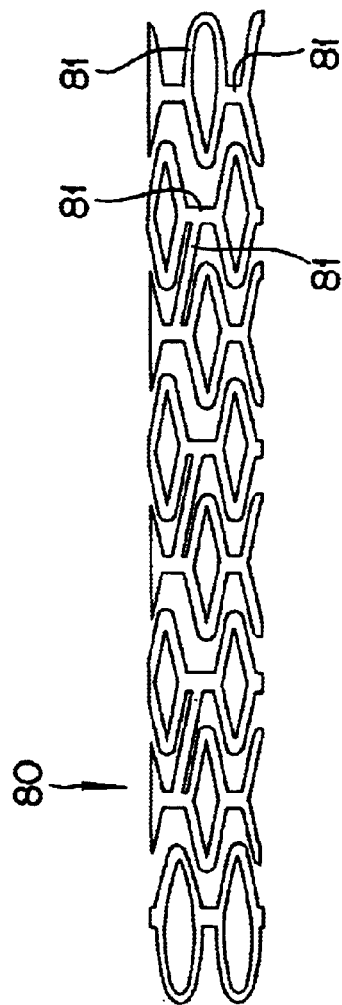
FIG. 9 is a partially omitted sectional view of the stent of this invention as one embodiment.
Figure 10:
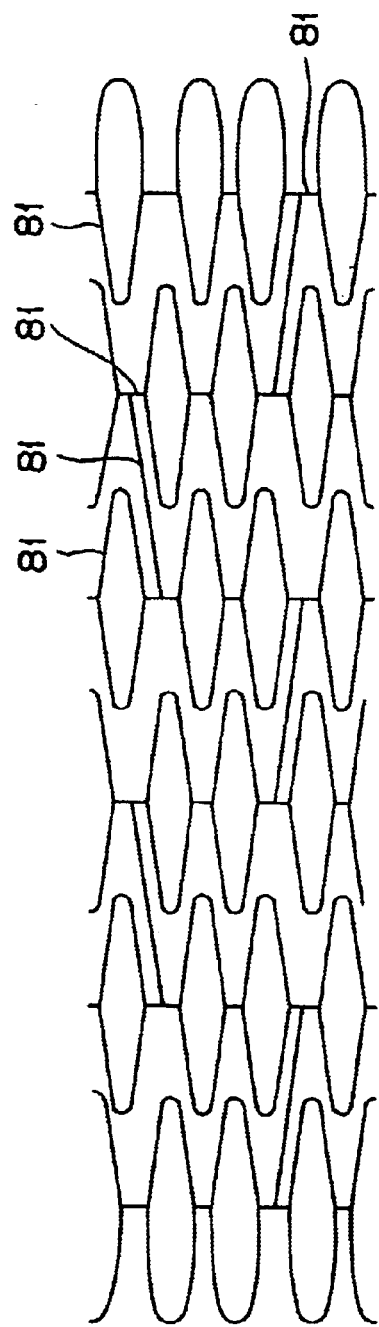
FIG. 10 is an expansion plan of the stent illustrated in FIG. 9 as held prior to dilation.

Example 5 of alloy shown in Table 1, namely the Ti-36.2Zr-12.3Nb-12.0Ta-7.9Sn alloy (% by weight), was manufactured into a pipe. The details of the method for producing a stent and the structural design thereof are similar to those disclosed in U.S. Pat. No. 5,879,381. In summary, the pipe of 1.4 mm in outer diameter and 0.10 mm in wall thickness was cut to a length of 50 mm and the pattern of a stent illustrated in the expansion plan of FIG. 10 was formed on the pipe with a YAG laser. The pipe was deburred and subjected to surface polishing to produce a stent 80 in the shape illustrated in the partially omitted sectional view of FIG. 9. A stent strut 81 was finished so as to measure 0.15 mm in width and 0.08 mm in wall thickness. Various other designs are available for the stent. Varying shape designs and varying methods of production can be suitably utilized. For example, the manufacture may be attained by a method which comprises steps of punching a stent pattern in a flat stainless steel sheet, forming a tube therefrom, and welding the seam. For the operation of punching the stent pattern, an etching method called photo-ablication which uses a masking and a chemical reagent, a electrical discharge machining method which uses a dye, and a mechanical cutting method are available. Besides the slotted type, a stent of mesh type using a wire and a stent of a coil type can be made easily from the material of this invention. Since the Ti—Zr alloy of this invention can be subjected to cold working, it can be easily adapted for the stent design and working method which precondition the conventional stainless steel materials and Ta and can be applied to various types of stents.

Figure 11:
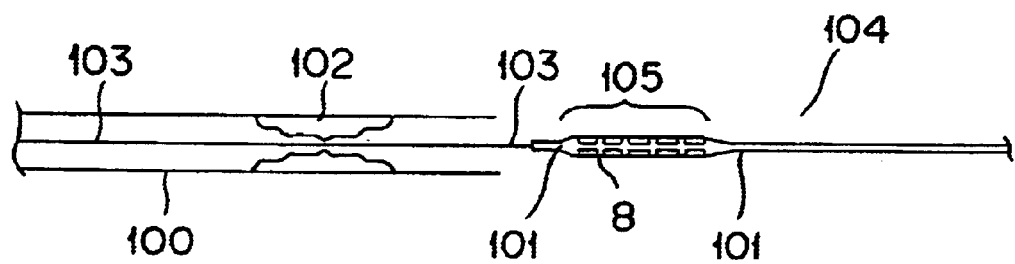
FIG. 11 is a diagram illustrating a state in which the stent is inserted.

From Example 5 of alloy of this invention shown in Table 1, a stent 80 having a strut thickness of 80 microns was manufactured. The stent 80 was mounted on a balloon 101, transported to a porcine left coronary artery (LAD #6) as illustrated in FIG. 11, and retained at a prescribed site by inflating the balloon 101. A guide wire 103 had been passed in advance through a blood vessel 100 and a narrow part 102 of the blood vessel and a stent system 104 was inserted along the guide wire 103. FIG. 11 is an explanatory diagram of the stent technique.

Since the stent 80 of this invention manifested only one quarter of the elasticity of a conventional stent made of stainless steel in the same design, the stent 80 itself enjoyed enhanced flexibility, an inflation balloon part 105 in its entirety of the stent system 104 formed of a delivery balloon plus the stent was allowed to acquire enhanced flexibility, and thus the delivery of the stent even to a tortuous blood vessel having strict bending was further facilitated. That is, since the stent 80 of this invention excelled in flexibility, it could be transported even along a tortuous blood vessel to a prescribed site and then retained therein. Since the stent 80 of this invention manifested significantly low elasticity as compared with stainless steel (JIS SUS316L) as a conventional material, it enjoyed outstanding comformability to the shape of the blood vessel. Further, the stent 80 manifested mechanical strength equal to or higher than that of the stainless steel (JIS SUS316L) and exerted no adverse effects on the power for retaining the inflation of the balloon. The visibility of this alloy under the X-ray fluoroscopy was as high as expected and was numerically equivalent to about 24 microns of pure gold. It manifested contrast and opaqueness twice as high as that of the ribs and allowed clear discrimination from the backbone. The struts 81 of the stent 80 could be visually confirmed. As regards this point, it has been clinically pointed out that a conventional stent formed of stainless steel is totally invisible from the viewpoint of X-ray contrast and opaqueness and it inhibits accurate decision of the position for its retention. Thus, the stent of this invention may be justly rated as highly preferable. Even the stent made of stainless steel may be made visible by increasing the wall thickness thereof extremely, it is self-evident that the increase in the thickness will result in impairing the flexibility of stent and degrading the capability of delivery. The stent 80 of this invention has X-ray contrast and opaqueness equivalent to 24 microns of gold even on the backbone and, therefore, can be distinguished from a tissue of human body. When a contrast medium is injected to a blood vessel in the confirmatory angiography, the flow of the contrast medium can be observed. The stent 80 manifests X-ray contrast and opaqueness equivalent to about 24 microns of gold and manifest X-ray contrast and opaqueness enough to be seen through. It can be predicted, therefore, to permit clear observation of the flow of a contrast medium having high contrast equivalent to about 50 microns of gold. Conversely, the confirmation may not be easily attained when a contrast medium of low opaqueness is passed to a site where X-ray opaqueness is manifested strongly. The conventional stent made of Ta as a material requires the struts thereof to have such a large diameter as of the order of 130 microns and a fair thickness for the sake of retention of strength and, therefore, possesses X-ray contrast and opaqueness equivalent to about 100 microns of gold. That is to say, the conventional stent has the problem that the inner cavity of the stent is invisible because it appears more clearly than necessary and produces unduly strong contrast. As a result, the passing of a contrast medium of a poor X-ray opaqueness could not be actually observed. Further, it has another problem that the inner diameter of the stent in the inflated state cannot be measured because the interior thereof is not seen through and that the question whether or not the stent is re-narrowed cannot be easily confirmed by passing a contrast medium. In these circumstances, the desirability of developing a stent having a proper contrast and opaqueness permitting discrimination from bones and allowing the passing of the contrast medium to be observed has been finding growing recognition. The stent 80 of this invention has been confirmed to manifest X-ray contrast and opaqueness sufficient to be significantly different from the contrast medium and have proper contrast and opaqueness enough to be seen through. Further, the stent 80 made of the Ti—Zr type alloy of this invention combines long-term biocompatibility, excellent workability, high strength, and flexibility and forms an ideal stent to be implanted safely.

EXAMPLE 10

Heparin Coating Stent

A surface of a stent 80 of this invention manufactured in the same manner as in Example 9 was coated with heparin by following the procedure disclosed in EP-A-832,618. The covalent bond with heparin of the surface of the stent in the method disclosed in EP-A-832,618 was attainable because the stent 80, which was made of an easily oxidizable metallic material composed of Ti, Zr, Nb, Ta, etc., allowed the surface thereof to be oxidized with ozone and utilized for easy ligation with a coupling agent, consequently permitted the reaction of aminated heparin to form a covalent bond with heparin thereof. The effect by the heparin coating was confirmed by an animal experiment that the anti-thrombogenicity thereby was equivalent to that which is obtained by a stent made of stainless steel and coated with heparin as disclosed in of EA-A-832,618.

EXAMPLE 11

Guide Wire

Physical properties demanded by a material for a guide wire to be used as a guiding tool of a catheter are described in detail in JP-B-03-015,914. A Ni—Ti-superelastic alloy and an amorphous alloy have been proposed as a material fit for the guide wire. The alloy of this invention is likewise suitable for the guide wire because it manifests low elasticity and high strength and high springiness.

Further, the use of the Ti—Zr alloy of this invention particularly allows manufacture of a microguide wire because it is capable of remarkably improving X-ray contrast and opaqueness as compared with a conventional alloy.

As a matter of course, it can be used for a spring type guide wire disclosed in JP-B-62-020,827 and a plastic-coated type guide wire having a tip of relatively low rigidity disclosed in U.S. Pat. No. 4,925,445 and JP-B-02-024,550.

As one preferable example, the application of the alloy to a microguide wire described herein below will be described with annotation. As typical examples of a very thin microguide wire, a wire using a Ni—Ti superelastic alloy as a core and a wire using a core of stainless steel may be cited. Since the material of core itself is deficient in X-ray contrast and opaqueness, a wire having an outer diameter of not more than 0.016 inch has been devised to compensate for visibility under the X-ray fluoroscopy as by being coated with a resin incorporating therein a contrast filler or being painted with a contrast marker, for example. Physicians, however, have demanded a guide wire of a still smaller outer diameter of 0.010 inch or 0.007 inch. Thus, the contrast marker or the contrast layer in such a case is inevitably required to decrease the thickness of the guide wire extremely. In this case, if the core of the guide wire itself has no contrast and opaqueness, the guide wire would become invisible. Further, a guide wire must have enough flexibility and spring elasticity because it needs to be inserted in a tortuous blood vessel. It is further required to transfer torque of the wire to a distal part from the basal end as retained in the bent state for the purpose of selecting a target blood vessel.

Figure 12:
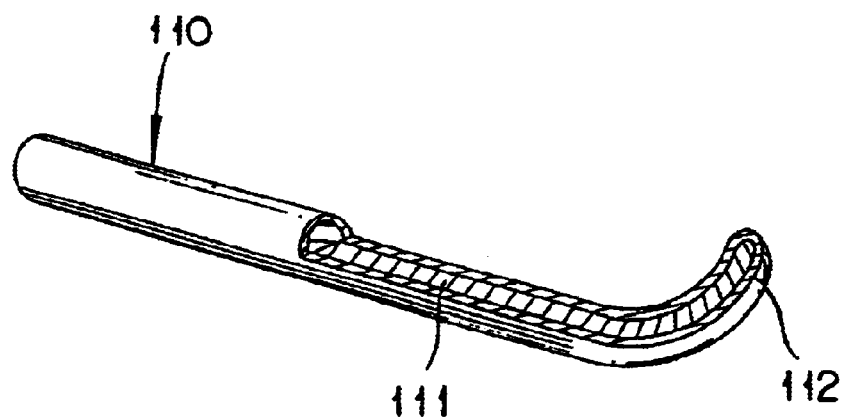
FIG. 12 is a perspective partially sectioned diagram of the guide wire of this invention as one embodiment.

Example 4 of alloy of this invention indicated in Table 1, namely the Ti-34.4Zr-11.7Nb-22.7Ta-1.2Au alloy (% by weight), was obtained by adding 1.2% by weight of pure gold as a second additive element to the alloy of Example 1 of alloy as a mother alloy. A guide wire 110 illustrated in the partially sectional perspective view of FIG. 12 was manufactured by using a core 111 made of the alloy of Example 4 of alloy. The core 111 was partially coated with a coating resin 112 having a contrast medium incorporated by kneading therein over a length of 30 cm from the tip thereof, with the operating proximal part of the guide wire 110 left uncoated as the alloy base (not shown). On the surface of the tip resin, was coated a hydrophilic coating resin adapted to manifest lubricity on exposure to moist as disclosed in U.S. Pat. No. 4,876,126 (not shown). A guide wire measuring 0.007 inch in outer diameter of the proximal part, 0.007 inch in outer diameter of the tip part, and 0.05 mm in core diameter of the flexible tip part and manufactured by using Example-4 of alloy of this invention could be observed under X-ray fluoroscopy because the alloy itself which constitutes the core manifest contrast and opaqueness equivalent to about 25 microns of gold. The visibility under X-ray fluoroscopy of the guide wire of this invention as actually observed was equivalent to 30 microns of gold because the guide wire was provided with a resin coating phase containing an X-ray contrast medium. The decrease in a core diameter of a conventional guide wire at the tip part thereof had heretofore realized the limitations because of the problem of the visibility of the guide wire and the deficiency in the tensile strength due to the decrease in diameter. In contrast, the diameter of the guide wire made of Example-4 of alloy of this invention could be decreased safely because of its high tensile strength as of 1500 Mpa. Further, since it possessed as high three-point bending strength as 2500 Mpa in spite of such a low elasticity as of a Young's modulus of 65.2 Gpa, it proved most suitable for a guide wire enjoying flexibility, strength, and impact resilience. This alloy, when used as a guide wire 110, exhibited veritably ideal properties in terms of torque transmitting property and strength of body.

EXAMPLE 12

Centrifugal Pump Type Left Ventricular Assisting Device

Figure 13:
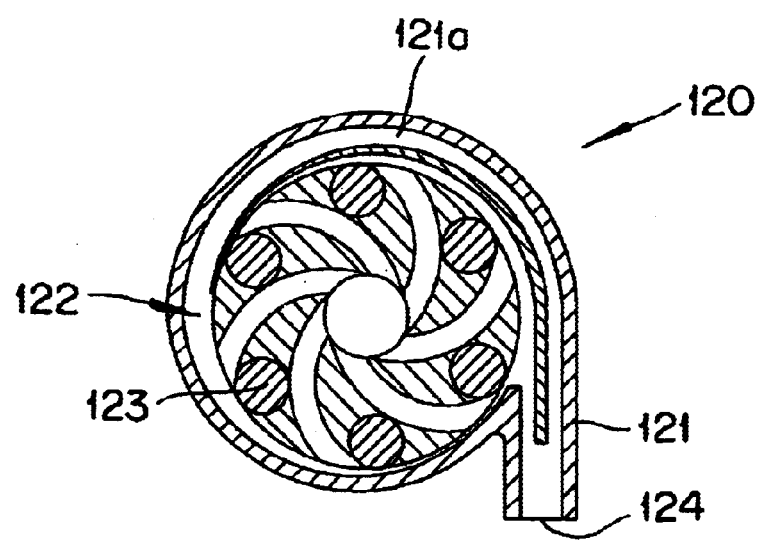
FIG. 13 is a cross section of the main centrifugal pump part of the left ventricular assisting device of this invention as one embodiment as taken across the impeller part.

A left ventricular assisting device 120 of the centrifugal pump type disclosed in EP-A-810,374 was manufactured by using Example-2 of alloy of this invention indicated in Table 1, namely the Ti-29.8Zr-12.1Nb-23.6Ta alloy (% by weight). FIG. 13 is a cross section of the left ventricular assisting device of this example taken through the impeller part thereof. A housing 121 shown in FIG. 13 was manufactured by using Example-2 of alloy of this invention. A flow path 121a and an impeller 122 which were fated to contact directly with blood inside the housing were coated with heparin in the same manner as disclosed in EP-A-832,618. The impeller 122 was equipped with a permanent magnet 123 so as to utilize magnetic floatation as a driving force. By an external electromagnet (not shown) disposed on the housing, the permanent magnets 123 floated repulsively to impart rotation to the impeller 122 without the aid of a contact shaft. By the rotation with the impeller 122, the blood was supplied from an inflow port (not shown) and discharged through an outlet port 124. The members of the housing, therefore, must be non-magnetic and have magnetism transmitted effectively. Since a housing 121 has heretofore had a complicated shape, a material therefor has been started to be studied using a non-magnetic plastic material. During a long-term animal experiment, however, a breakage of a inflow or outflow port has been recognized due to degradation over time of the plastic material. The plastic material has proved unsatisfactory for a port which is a part for connection with the blood vessel and is subjected to repeated exertion of stress, on account of deterioration of strength in view of a possibility of protracted in vivo use. In consideration of these facts, therefore, a metallic material capable of being manufactured even in a complicated shape has been demanded. A pure Ti material was selected from the viewpoint of its biocompatibility and non-magnetism and the manufacture of a pure Ti alloy has been tried by the operation of cutting. Since the pure Ti manifested very poor cutting workability, however, the processing required nearly one week's time even by the use of a device operating with a very high rotational speed. Thus, the manufacture manifested poor productivity and proved very expensive. In contrast, the Ti—Zr alloy according to Example-2 of alloy excelled in rollability and mechanical workability and permitted combination of introduction of a press working of plate and a cutting working, and allowed a significant reduction in working time. This alloy manifested corrosion resistance at least on a par with the pure Ti and excelled in biocompatibility and could be put to use in a protracted implantation more safely than the pure Ti. The left ventricular assisting device 120 of this invention can be expected to allow mass production and cost cut owing to the excellent workability of the housing 121. Incidentally, the impeller 122 and other parts may be manufactured with the Ti—Zr alloy of this invention.

The entire disclosure of Japanese Patent Application Nos. 11-116,225, 11-375,057, and 11-375,058 filed on Apr. 23, 1999, Dec. 28, 1999, and Dec. 28, 1999, respectively, including specification, claims, drawings and summary are incorporated herein by reference in its entirety.

What is claimed is:

1. A β-phase Ti—Zr type alloy having a body-centered cubic lattice structure and which consists of 25 to 50% by weight of Ti, 25 to 60% by weight of Zr, 5 to 30% by weight of Nb, and 5 to 40% by weight of Ta, provided that the weight ratio of Zr to Ti be in the range of 0.5 to 1.5 and the weight ratio of Nb to Ta be in the range of 0.125 to 1.5.

2. A β-phase Ti—Zr type alloy having a body-centered cubic lattice structure and which consists of 25 to 50% by weight of Ti, 25 to 60% by weight of Zr, 5 to 30% by weight of Nb, and 5 to 40% by weight of Ta, provided that the weight ratio of Zr to Ti be in the range of 0.5 to 1.5 and the weight ratio of Nb to Ta be in the range of 0.125 to 1.5, wherein at least one of Nb or Ta is substituted by at least one first substituent element selected from the group consisting of Ni, Cu, Pd, Pt, Al, Si, Cr, Mn, Co, V, Fe, Ag, Au, Sn, Mo, Hf, Zn, Ga, W, Tc, Ru, Rh, Cd, and In.

3. A Ti—Zr type alloy according to claim 1, wherein said Ti—Zr type alloy has incorporated therein at least one first additive element selected from the group consisting of Ni, Cu, Pd, Pt, Al, Si, Cr, Mn, Co, O, N, V, Fe, Ag, Au, Sn, Mo, and Hf in an amount in the range of 0.01 to 5% by weight, based on the total weight of the component elements.

4. A medical appliance which comprises a part formed of a β-phase Ti—Zr type alloy having a body-entered cubic lattice structure and which consists of 25 to 50% by weight of Ti, 25 to 60% by weight of Zr, 5 to 30% by weight of Nb, and 5 to 40% by weight of Ta, provided that the weight ratio of Zr and Ti fall in the range of 0.5 to 1.5 and the weight ratio of Nb to Ta fall in the range of 0.125 to 1.5.

5. A medical appliance which comprises a part formed of a β-phase Ti—Zr type alloy having a body-centered cubic lattice structure and which consists of 25 to 50% by weight of Ti, 25 to 60% by weight of Zr, 5 to 30% by weight of Nb, and 5 to 40% by weight of Ta, provided that the weight ratio of Zr and Ti fall in the range of 0.5 to 1.5 and the weight ratio of Nb to Ta fall in the range of 0.125 to 1.5, wherein a part of Zr is substituted by Sn and the content of said Sn is in the range of 5 to 10% by weight, based on the total weight of the component elements.

6. A medical appliance which comprises a part formed of a β-phase Ti—Zr type alloy having a body-centered cubic lattice structure and which consists of 25 to 50% by weight of Ti, 25 to 60% by weight of Zr, 5 to 30% by weight of Nb, and 5 to 40% by weight of Ta, provided that the weight ratio of Zr and Ti fall in the range of 0.5 to 1.5 and the weight ratio of Nb to Ta fall in the range of 0.125 to 1.5, wherein at least one of Nb or Ta is substituted by at least one second substituent element selected from the group consisting of Pd, Pt, and Au.

7. A medical appliance according to claim 4, wherein said alloy has incorporated therein at least one second additive element selected from the group consisting of Pd, Pt, and Au in an amount in the range of 0.01 to 5% by weight, based on the total weight of the component elements.

8. A guide wire which comprises a functional main body formed of the Ti—Zr type alloy set forth in claim 4.

9. A stent which comprises a functional main body formed of the Ti—Zr type alloy set forth in claim 4.

10. A ventricular assisting device which comprises a functional main body formed of the Ti—Zr type alloy set forth in claim 4.

11. A medical appliance destined to contact with blood, which comprises a functional main body formed of said Ti—Zr type alloy set forth in claim 4, and has heparin covalently bound to the surface of the alloy destined to contact with blood.

12. A medical appliance according to claim 11, wherein said appliance is a guide wire, a stent, or a ventricular assisting device.

13. A Ti—Zr type alloy according to claim 1, wherein the alloy includes at least 10% Nb and/or 10% Ta.

14. A Ti—Zr type alloy according to claim 2, wherein the alloy includes at least 10% Nb and/or 10% Ta.

15. A medical appliance according to claim 4, wherein the alloy includes at least 10% Nb and/or 10% Ta.

16. A medical appliance according to claim 5, wherein the alloy includes at least 10% Nb and/or 10% Ta.

17. A Ti—Zr type alloy according to claim 1, wherein the alloy includes at least 10% Nb and at least 10% Ta.

18. A Ti—Zr type alloy according to claim 2, wherein the alloy includes at least 10% Nb and at least 10% Ta.

19. A medical appliance according to claim 4, wherein the alloy includes at least 10% Nb and at least 10% Ta.

20. A medical appliance according to claim 5, wherein the alloy includes at least 10% Nb and at least 10% Ta.

* * * * *